United States Patent [19]

Campbell et al.

[11] 4,406,897
[45] Sep. 27, 1983

[54] 6-ARYL-4-HYDRAZINYL-S-TRIAZIN-2-ONES

[75] Inventors: Henry F. Campbell; Thomas H. Scholz, both of Lansdale; George H. Douglas, Malvern, all of Pa.

[73] Assignee: William H. Rorer, Inc., Fort Washington, Pa.

[21] Appl. No.: 280,808

[22] Filed: Jul. 6, 1981

[51] Int. Cl.³ .................. C07D 251/16; C07D 251/42; A61K 31/53; C07D 413/04
[52] U.S. Cl. ............................ 424/246; 424/248.4; 424/248.5; 424/249; 544/58.6; 544/209; 544/113; 544/194; 544/211; 544/212
[58] Field of Search ............... 544/194, 211, 212, 113, 544/209, 58.6; 424/249, 246, 248.4, 248.5

[56] References Cited

U.S. PATENT DOCUMENTS 3,700,671 10/1972 D'Alelio .............................. 544/212
4,246,409 1/1981 Douglas et al. .................... 544/211

Primary Examiner—John M. Ford
Attorney, Agent, or Firm—James A. Nicholson; Alexis Barron; Martin F. Savitzky

[57] ABSTRACT

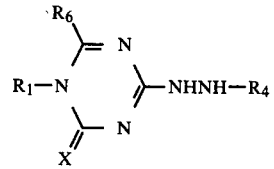

This invention relates to 6-aryl-4-hydrazinyl-1,2-dihydro-1,3,5-triazin-2-ones and 2-thiones of Formula I, processes for their preparation, intermediates useful in said processes and methods of treating physiological disorders in humans and animals, in particular, cardiovascular disorders, including hypertension.

16 Claims, No Drawings

6-ARYL-4-HYDRAZINYL-S-TRIAZIN-2-ONES

FIELD OF THE INVENTION

This invention relates to s-triazin-2-one and thione compounds, processes for their preparation, intermediates useful in their preparation, pharmaceutical compositions and methods for influencing physiological function, such as, blood pressure in humans and animals.

REPORTED DEVELOPMENTS 1,3,5-triazine compounds are known to possess a broad spectrum of biological activity. The 4,6-diamino-1,2-dihydro-2-triazines have been reported to be effective as antimalarial, antitumor, antihelminthic and antibacterial agents as well as active agents against coccidosis in chicks and against murine toxoplasmosis. See *Heterocyclic Compounds*, Volume 7, John Wiley & Sons, 1961 (Elderfield ed.) Chapter 8, "S-Triazines."

The antiherbicidal activity of 1-alkyl-4-alkylamino-1,2-dihydro-2-triazin-2-ones and thiones has been reported in U.S. Pat. No. 3,585,197 to Seidel et al. Recently, 1-aryl-1,2-dihydro-1,3,5-triazin-2-ones (thione) and their pharmacological uses have been reported in U.S. Pat. No. 4,246,409 to Douglas et al.

s-Triazin-2-ones (thiones) which are substituted by hydrazinyl groups in the 4-position have not been previously reported.

SUMMARY OF THE INVENTION

This invention relates to a class of s-triazine compounds according to Formula I

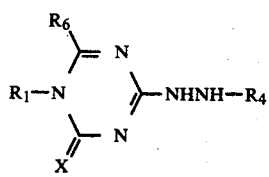

wherein:
  X is oxygen or sulfur;
  R₁ is hydrogen, alkyl, cycloalkyl, alkenyl, alkynyl or aralkyl;
  R₄ is hydrogen, alkyl, cycloalkyl, alkenyl, alkynyl, alkanoyl, carboalkoxy, carbamoyl, alkyl carbamoyl, aryl, aroyl, aralkyl, heterocyclic, substituted heterocyclic, halo alkyl, or halo alkanoyl;
  R₆ is aryl, substituted aryl, aralkyl, heterocyclic, substituted heterocyclic, heterocyclic lower alkyl, or substituted heterocyclic lower alkyl;
and the pharmaceutically acceptable acid addition salts thereof.

This invention relates also to processes for the preparation of compounds of Formula I and intermediate compounds useful in these processes.

Compounds of Formula I possess pharmaceutical activity, including cardiovascular activity, such as, blood pressure lowering activity and are useful in methods of treating physiological disorders, such as, hypertension in humans and animals.

DETAILED DESCRIPTION OF THE INVENTION

Depending upon the specific substitution, compounds of Formula I above may be present in enolized or tautomeric forms. Certain of the compounds can also be obtained as hydrates or in different polymorphic forms. The structures used herein to designate novel compounds are intended to include the compound along with its alternative or transient states. The nomenclature generally employed to identify the novel triazine derivatives as disclosed herein is based upon the ring structure shown in Formula I with the triazine ring positions numbered counterclockwise beginning with the nitrogen having the R₁ substitution.

When R₁ is hydrogen, the predominate tautomeric form of hydrazinyl compounds according to this invention can be depicted by Formula I-a.

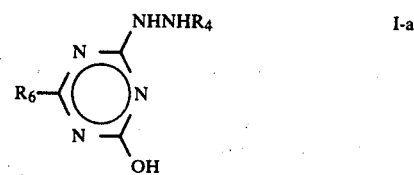

The predominate tautomeric form of triazine compounds useful as intermediates in the process of this invention can be depicted by Formulae II and III.

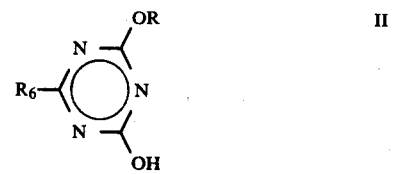

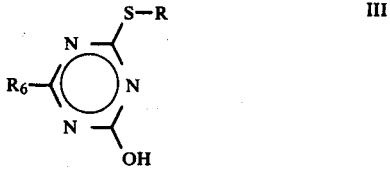

Compounds of this invention which are preferred include those according to Formula I wherein:
  X is oxygen or sulfur;
  R₁ is hydrogen or lower alkyl;
  R₄ is hydrogen, lower alkyl, cycloalkyl, lower alkenyl, lower alkynyl, lower alkanoyl, carboalkoxy, carbamoyl, alkyl carbamoyl, aryl, aroyl, aralkyl, heterocyclic, substituted heterocyclic, halo lower alkyl, or halo lower alkanoyl;
  R₆ is phenyl, substituted phenyl, heterocyclic, substituted heterocyclic, heterocyclic lower alkyl or substituted heterocyclic lower alkyl;
and the pharmaceutically acceptable acid addition salts thereof.

A subclass of these compounds, of particular interest, includes compounds according to Formula I wherein:
  X is oxygen or sulfur;
  R₁ is hydrogen or lower alkyl;
  R₄ is hydrogen, lower alkyl, lower alkanoyl, or halo lower alkanoyl;
  R₆ is phenyl or substituted phenyl;
wherein: substituted phenyl means phenyl in which one or more of the phenyl hydrogens has been replaced by the same or different substituents selected from the group consisting of halo, lower alkoxy, lower alkyl, halo lower alkyl, nitro, amino, lower alkanoyl, hydroxy, carbo lower alkoxy, phenyl lower alkoxy, lower alkylacyloxy, cyano, halo lower alkoxy and lower alkyl sulfonyl;
and the pharmaceutically acceptable acid addition salts thereof.

The preferred compounds of this subclass are those where:
R₁ is hydrogen or lower alkyl;
R₄ is hydrogen, lower alkyl, lower alkanoyl, phenyl, benzoyl, carboloweralkoxy, substituted phenyl, pyridyl or substituted pyridyl;
R₆ is phenyl or substituted phenyl;
and the pharmaceutically acceptable acid addition salts thereof.

The most preferred compounds of this invention are those where:
R₁ is hydrogen;
R₄ is hydrogen, methyl or acetyl, and;
R₆ is phenyl or substituted phenyl; provided that when R₆ is substituted phenyl the phenyl substituent is either halo or alkyl;
and the pharmaceutically acceptable acid addition salts thereof.

A special embodiment of this most preferred class of compounds are those where:
R₆ is phenyl substituted in either or both of the meta positions by a halogen, for example, chloro.

An embodiment of this invention, of particular interest, is a 4-hydrazinyl triazinone according to Formula I wherein R₆ is a heterocyclic ring. The most preferred heterocyclic ring is pyridyl and the exemplary subclass of the compounds according to this invention which include the pyridyl ring are shown below in Formulae IV-VI.

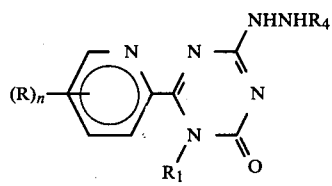   IV

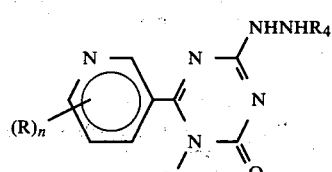   V

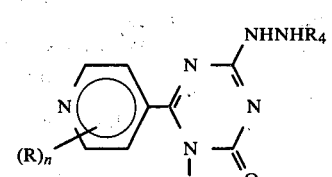   VI wherein:
n is zero to four;
R is alkyl, alkoxy, halo, cyano, amino, carbamoyl, alkylamino, or dialkylamino; and
X, R₁ and R₄ are as defined above.

As employed above and throughout the disclosure, the following terms, unless otherwise indicated, shall be understood to have the following meanings:

"Alkyl" means a saturated aliphatic hydrocarbon which may be either straight- or branched-chain. Preferred are lower alkyl groups which have up to about 6 carbon atoms, including methyl, ethyl and structural isomers of propyl, butyl, pentyl, and hexyl.

"Cycloalkyl" means a saturated cyclic hydrocarbon, preferably having about 3 to about 6 carbon atoms, which may also be substituted with a lower alkyl group.

"Carbamoyl" means a radical of the formula

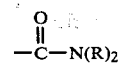

where R may be hydrogen or lower alkyl.

"Alkenyl" means an unsaturated aliphatic hydrocarbon which may include straight or branched chains. Preferred groups have up to about 6 carbon atoms and may be vinyl and any structural and geometric isomers of propenyl, butenyl, pentenyl, and hexenyl.

"Alkynyl" means an unsaturated aliphatic hydrocarbon containing one or more triple bonds. Preferred groups contain up to about 6 carbon atoms and include ethynyl, propynyl, butynyl, pentynyl, and hexynyl.

"Aryl" means a radical of an aromatic group. The preferred aromatic groups are phenyl and substituted phenyl.

"Substituted phenyl" means a phenyl group in which one or more of the hydrogens has been replaced by the same or different substituents including halo, lower alkyl, halo lower alkyl, nitro, amino, acylamino, hydroxy, lower alkoxy, aryl lower alkoxy, acyloxy, cyano, halo lower alkoxy or lower alkyl sulfonyl.

"Aralkyl" means lower alkyl in which one or more hydrogens is substituted by aryl (preferably phenyl or substituted phenyl). Preferred groups are benzyl or phenethyl.

"Heterocyclic" or "heterocyclic ring" means a cyclic or bicyclic system having 1 to 3 hetero atoms which may be nitrogen, oxygen or sulfur, including oxazolidinyl, thiazolidinyl, pyrazolidinyl, imidazolidinyl, piperidyl, piperazinyl, thiamorpholinyl, 1-pyrrole, 2-pyrrole, 3-pyrrole, 2-furan, 3-furan, 2-thiophene, 3-thiophene, 2-tetrahydrothiophene, 3-tetrahydrothiophene, 1-imidazole, 2-imidazole, 4-imidazole, 5-imidazole, 2-oxazole, 4-oxazole, 5-oxazole, 2-thiazole, 4-thiazole, 5-thiazole, 1-pyrazole, 3-pyrazole, 4-pyrazole, 5-pyrazole, 1-pyrrolidine, 2-pyrrolidine, 3-pyrrolidine, 2-pyridyl, 3-pyridyl, 4-pyridyl, 2-pyrimidine, 4-pyrimidine, 5-pyrimidine, 6-pyrimidine, 2-purine, 6-purine, 8-purine, 9-purine, 2-quinoline, 3-quinoline, 4-quinoline, 5-quinoline, 6-quinoline, 7-quinoline, 8-quinoline, 1-isoquinoline, 3-isoquinoline, 4-isoquinoline, 5-isoquinoline, 6-isoquinoline, 7-isoquinoline, 8-isoquinoline, carbazole, trimethylenetriaminyl ethyleneiminyl and morpholinyl;

"Substituted heterocyclic" or "substituted heterocyclic ring" means a heterocycle in which one or more of the hydrogen on the ring carbons have been replaced by substituents as given above with respect to substituted phenyl.

Preferred heterocyclic rings are pyridyl, pyrimidyl, pyrazolyl, imidazolyl, furyl, thienyl, oxazolyl, thiazolyl, piperidyl, morpholinyl, oxazolidinyl, thiazolidinyl, pyrazolidinyl, imidazolidinyl, piperazinyl, thiamorpholinyl, trimethylenetriaminyl and ethyleneiminyl.

The terms "halo" and "halogen" include all four halogens, namely, fluorine, chlorine, bromine and iodine. The halo alkyls, halophenyl and halo-substituted pyridyl include groups having more than one halo substituent which may be the same or different such as trifluoromethyl, 1-chloro-2-bromo-ethyl, chlorophenyl, 4-chloropyridyl, etc.

"Acyloxy" means an organic acid radical of lower alkanoic acid such as acetoxy, propionoxy, and the like.

"Lower alkanoyl" means the acyl radical or a lower alkanoic acid, including acetyl, propionyl, butyryl, valeryl, and stearoyl.

"Alkoxy" means the oxy radical of an alkyl group, preferably a lower alkyl group, such as methoxy, ethoxy, n-propoxy, and i-propoxy.

"Aroyl" means a radical of the formula

wherein R is aryl. Preferred aroyl groups include benzoyl and substituted benzoyl.

The preferred "halo lower alkyl" group is trifluoromethyl.

The preferred "halo lower alkanoyl" group is trifluoroacetyl.

The compounds of this invention may be prepared by the general synthesis according to Scheme I:

Scheme I

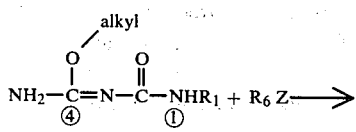

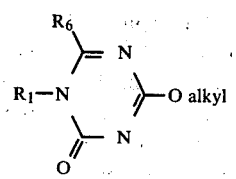

A 1-$R_1$-substituted-4-alkyl isobiuret is cyclized to the corresponding 1-$R_1$-6-$R_6$-4-alkoxy-1,2-dihydro-1,3,5-triazin-2-one by treatment with an $R_6$ substituted cyclizing reagent.

The group in the 4-position of the isobiuret, shown as O-alkyl, may be any suitable group which is capable of being displaced upon treatment of the cyclized product with a hydrazinyl reagent. The alkoxy groups, as shown in Scheme I, are preferred in this method.

Condensation of the 4-alkoxy triazinone with an appropriately substituted hydrazine produces the 4-hydrazino adduct according to Scheme II:

Scheme II

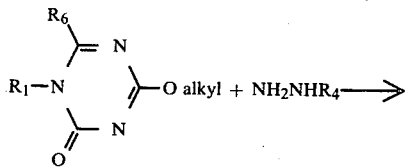

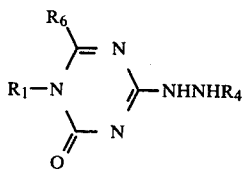

Alternatively, the 4-alkoxy-s-triazinone may be reacted with unsubstituted hydrazine thereby producing the 4-hydrazinyl triazinone which may be treated with an appropriate alkylating or acylating reagent such as an alkyl halide, alkyl triflate, alkanoyl halide, such as, benzoyl halide, methyl halide, acetyl chloride, benzoyl chloride, and result in the desired $R_4$ substitution.

The triazinthione compounds according to this invention are prepared by the same general route by utilizing the corresponding isothiobiuret as starting material.

The isobiuret (isothiobiuret) starting material may be prepared by any manner known to those skilled in the art. One process for the synthesis of these particular isobiurets (isothiobiuret) comprises the treatment of an O-alkylisourea (isothiourea), such as O-methyl-isourea, with an appropriately substituted isocyanate (isothiocyanate) according to Scheme III:

Scheme III

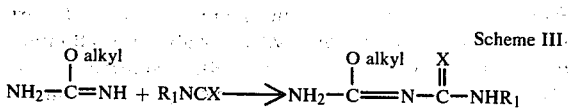

For example, O-methyl isourea may be prepared in situ by neutralizing O-methyl isourea hydrogen sulfate with one equivalent of base, such as sodium hydroxide, in a polar nonaqueous solvent, such as, THF or ethanol. The reaction media is dried before adding the isocyanate by addition of a drying agent such as sodium sulfate ($Na_2SO_4$). The isocyanate is added to the reaction media dropwise and the isobiuret recovered by extraction and recrystallization.

The isocyanate may be prepared from primary alkyl amines or anilines by methods known to those in the art (e.g., reaction with phosgene or thiophosgene in the customary manner).

The cyclizing reagent may consist of an activated form of an acid amide or ortho ester or acyl derivative such as a Vilsmier reagent which will bring about acylation and ring closure of the isobiuret or isothiobiuret to give the corresponding s-triazinone or thione of the type described above.

The cyclizing reagent employed in the reaction can be any cationic reagent system capable of generating in the reaction mixture a stabilized carbonium ion having the oxidation state of an acid or acid amide. Since the cationic carbon is incorporated into the ring the choice of reagent will determine the $R_6$ substitution in the compounds of Formula I above. Thus, in the case of a dialkyl carboxylic acid amide dialkyl acetal, such as, dialkyl benzamide dialkyl acetal, $R_6$ is phenyl and the resulting triazine is substituted in the 6-position by phenyl; in the case where the nicotanamide derivative is used as the cyclizing reagent, $R_6$ is pyridyl and the resulting triazine is substituted in the 6-position by pryidyl.

In general, the preferred cyclizing reagents are the ortho esters of carboxylic acids of the Formula VII.

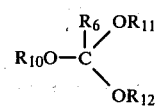

VII wherein:
$R_6$ is aryl, substituted aryl, aralkyl, heterocyclic, substituted heterocyclic, heterocyclic lower alkyl, or substituted heterocyclic lower alkyl; and
each of $R_{10}$ through $R_{12}$ are lower alkyl or halo lower alkyl.

Exemplary ortho esters include triethylorthobenzoate and trimethylortho-3-chlorobenzoate. Additional cyclizing reagents include the benzoic acid amide dialkyl acetals, such as, dialkyl benzamide dialkyl acetal, preferably, dimethyl benzamide dimethyl acetal; dialkyl nicotinamide dialkyl acetals, preferably, dimethyl nicotinamide dimethyl acetal; dialkyl phenylacetamide dialkyl acetal, preferably, dimethyl phenylacetamide dimethyl acetal. Other carboxylic acid amide derivatives can also be used including substituted derivatives.

Other methylidene derivatives that can be used as the cyclizing reagent include the combination of an N,N-disubstituted carboxylic acid amide any any strong alkylating agent preferably a strong methylating agent. Any of the strong alkylating agents known in the art such as methyliodide, methylfluorosulfonate, alkylmethane sulfonates, e.g., methylmethanesulfonate, and alkyl or dialkyl sulfates, e.g., dimethylsulfate can be suitably employed though dimethylsulfate is preferred owing to its ready availability. A cyclizing reagent, of particular interest, is a DMF-dimethylsulfate complex.

Reagents of the type shown in Formula VII above are stable products which are commercially available or can be prepared in advance.

The cyclizing reaction can be carried out by simply combining the reactants in a suitable solvent at room temperature with stirring. The reaction time can be shortened by heating the reaction mixture or by using elevated pressure or both. The solvent selected should have a relatively high boiling point and low vapor pressure in order to permit the reaction mixture to be heated above 100° C. The solvent that can be used include saturated and unsaturated hydrocarbons, aromatic solvents, alcohols such as methanol and ethanol, halogenated hydrocarbons such as chloroform, carbon tetrachloride, ethylene chloride, or others such as methyl acetate, ethyl acetate, acetonitrile, acetone, ether, acetamide, tetrahydrofuran and the like. Suitable mixtures of solvents can also be used. The reaction is preferably carried out under substantially anhydrous conditions though the presence of water can be tolerated. If small amounts of water are present, the effect can be offset by using an excess of the cyclizing reagent.

In carrying out the cyclizing reaction, the cyclizing reagent is preferably used in slight excess of the amount required as the stoichiometric equivalent of the isobiuret or isothiobiuret starting material. Reagent systems employing dimethyl sulfate are prepared as necessary for the cyclization or can be formed in situ in the reaction mixture by adding the reagent components to the reaction vessel in a suitable solvent or solvent mixture. When carrying out the cyclizing reaction with a reagent of the type shown in Formula VII, it is preferred to use as starting material an acid addition salt of the isobiuret or isothiobiuret or alternatively, if the free base is used, then an acid, preferably a mineral acid such as hydrochloric acid, can be added to the reaction mixture. When a reagent system comprising a carboxylic acid amide and a strong alkylating agent is employed, the reagent is itself acidic and the reaction proceeds readily with the free base as starting material. In such instances it may be advantageous to add a proton scavenging solvent such as a tertiary amine, e.g., triethylamine or cyclic amines such as pyridine. Other miscible solvents can be used along with the preferred amines e.g., solvents such as triethanolamine, acetonitrile, ethanol, etc., though dimethyl formamide is preferred.

The conversion of most isobiurets and isothiobiurets to the corresponding s-triazine derivative can be achieved in from less than about 20 minutes to about 5 hours at temperatures on the order of 100° C. to 120° C. Higher or lower temperatures can be used if desired, and the reaction can be carried out at room temperature.

In most cases the cyclized end product can be recovered by filtering after direct crystallization from the reaction mixture particularly where the solvent has been chosen to facilitate recovery of the end product. Where the product does not readily crystallize, the novel s-triazinone derivatives can be conveniently isolated in the pure form by solvent extraction using any of the usual organic solvents which are not miscible with water such as: the hydrocarbons, for example, hexane; the chlorinated hydrocarbons, for example, chloroform or carbon tetrachloride; the aromatic solvents such as benzene, xylene, toluene, o-chloro-toluene and the like; ethers such as dioxane; ketones such as 2-pentanone, etc. The s-triazinone product is extracted into the solvent layer generally after stripping the solvent or concentrating the reaction mixture then shaking with an extracting composition of water and solvent and removing the solvent component, leaving the by-product in the aqueous layer. The product is recovered by evaporating off the solvent. If desired, the product can be further purified by recrystallizing from a suitable organic solvent such as those noted above. The selection of solvent is not critical and generally those solvents which are most readily available will be employed.

Another method of preparing compounds according to this invention, where $R_1$ is hydrogen, is shown in Scheme IV where either of Routes 1 or 2 may be preferred.

Scheme IV

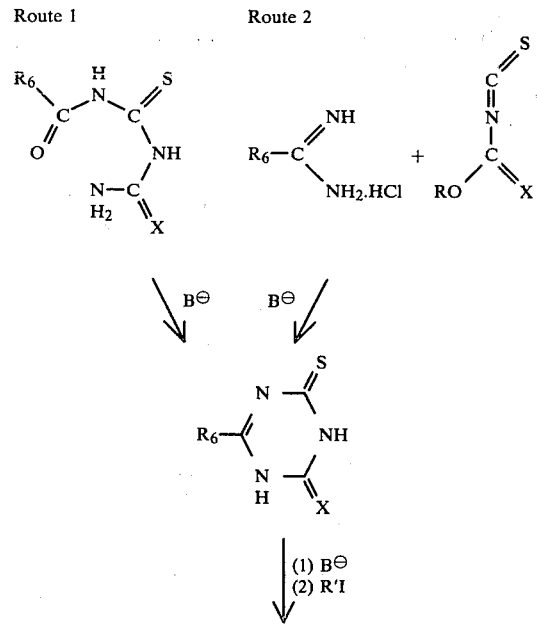

-continued
Scheme IV

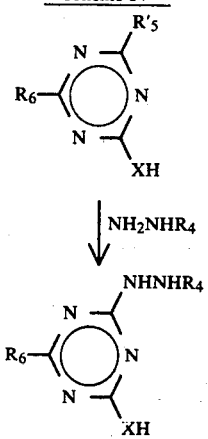

↓ NH₂NHR₄

According to Route 1, an N-carbonyl-N'-carbamoyl thiourea is cyclized, in the presence of base, to the corresponding 4-thio-triazin-2-one. The analogous thione may be prepared from the analogous thiocarbamoyl compound.

The N-carbonyl N'-carbamylthiourea may be prepared by reacting an appropriately substituted carbonyl isothiocyanate with urea according to Scheme V.

SCHEME V

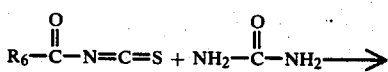

According to Route 2, an amidine is cyclized with an isothiocyanato alkoxy carbonyl in the presence of base.

The amidines are either known or may be synthesized according to known processes. The isothiocyanato compounds are either known or may be prepared by known processes, such as, treating an acyl or aroyl chloride with potassium isothiocyanate.

After the 4-thio-triazin-2-one (or thione) is formed, the desired hydrazinyl substituent may be introduced into the triazine ring by converting the thio group into a suitable leaving group, such as, an alkylated sulfur group, e.g. methylmercaptyl.

The compounds of this invention may be readily converted to their nontoxic acid addition salts by customary methods in the art. The nontoxic salts of this invention are those salts the acid component of which is pharmacologically acceptable in the intended dosages. Such salts would include those prepared from inorganic acids, and organic acids, such as, higher fatty acids, high molecular weight acids, etc. Exemplary acids include hydrochloric acid, hydrobromic acid, sulfuric acid, nitric acid, phosphoric acid, methane sulfonic acid, benzene sulfonic acid, acetic acid, propionic acid, malic acid, succinic acid, glycolic acid, lactic acid, salicylic acid, benzoic acid, nicotinic acid, phthalic acid, stearic acid, oleic acid, abietic acid, etc.

It is well known in the pharmacological arts that nontoxic acid addition salts of pharmacologically active amine compounds do not differ in activities from their free base. The salts merely provide a convenient solubility factor. Other salts, for example, quarternary ammonium salts, are prepared by known methods for quarternizing organic nitrogen compounds.

The following detailed examples show the synthetic preparation of certain compounds of this invention. They are to be construed as illustrations of the preparation of compounds according to this invention and not as limitations thereof.

EXAMPLE I

Preparation of 1-methyl-4-methylhydrazinyl-6-phenyl-1,2-dihydro-1,3,5-triazin-2-one Step 1

1,4-Dimethyl isobiuret 71.4 g of an aqueous NaOH solution are added to a stirred suspension of O-methylisourea hydrogen sulfate (76.38 g) in 500 ml of THF with cooling. After stirring for 15 minutes at room temperature, 200 g of anhydrous Na₂SO₄ are added to the mixture. The reaction mixture is filtered and 26.2 ml of methyl isocyanate in 100 ml of THF are added to the filtrate over a period of 1½ hours. The reaction mixture is stirred for an additional hour and then concentrated, ether added, and the resulting precipitate filtered and dried to give 48.40 g (83.9%) of isobiuret, m.p. 90°–92° C.

Step 2

4-Methoxy-1-methyl-6-phenyl-1,2-dihydro-1,3,5-triazin-2-one 1,4-dimethyl isobiuret (26.08 g) is suspended in trimethyl orthobenzoate (108.8 g). The suspension is stirred and heated to 140° C. for five hours while methanol is continuously removed from the reaction mixture. The reaction temperature is raised to 160° C. for two hours and then allowed to cool to RT overnight. Ethylacetate and hexane are added to the reaction mixture resulting in a precipitate which is filtered, washed with ether and dried to yield 7.00 g of triazinone (16.2%), m.p. 160°–162° C.

Step 3

4-Methylhydrazinyl-1-methyl-6-phenyl-1,2-dihydro-1,3,5-triazin-2-one 1.71 ml of methylhydrazine dissolved in 30 ml of methanol are added to a stirred solution of 4-methoxy-1-methyl-6-phenyl-1,2-dihydro-1,3,5-triazin-2-one in 100 ml of methanol. The mixture is stirred for one hour at RT and then refluxed for four hours. The reaction mixture is concentrated and the triazinone precipitated from ethyl acetate and hexane, filtered, washed with ether, and dried to yield 1.95 g of the desired product.

EXAMPLE II

Preparation of 4-methylhydrazinyl-1-methyl-6-phenyl-1,2-dihydro-1,3,5-triazin-2-one hydrochloride The precipitate, from step 3 of Example I above, is taken up in 750 ml of boiling ether. The solution is filtered through a cotton plug and allowed to cool to RT. Ether/HCl solution is added to the solution until precipitation ceases. The mixture is filtered, the solid washed with THF and ether and dried to yield 2.0 g of the hydrochloride, m.p. 127°–129° C.

EXAMPLE III

Preparation of
6-(4-Chlorophenyl)-2-hydroxy-4-methylhydrazinyl-1,3,5-triazine

Step 1

4-Chlorobenzoyl-isothiocyanate

A solution of 4-chlorobenzoyl chloride (127.1 ml) in 100 ml of dry toluene is added to a vigorously stirred suspension of dried KSCN (106.90 g) in about one liter of dried toluene. The reaction mixture is heated to reflux and after addition is completed the mixture is refluxed overnight. The reaction mixture is allowed to cool, KCl filtered and the filtrate evaporated leaving a reddish residue which solidifies on standing. The residue is vacuum distilled, using a steam filled condenser, yielding 152.4 g of a distillate, b.p. 88°–90° (0.350 torr).

Step 2

N-(4-chlorobenzoyl)-N'-carbamoyl thiourea

A solution of 4-Chlorobenzoylisothiocyanate (152.4 g) in THF (500 ml) is added dropwise to a stirred suspension of urea (46.3 g) in THF (750 ml). The reaction mixture is stirred over the weekend. The precipitate is filtered, washed with ether and dried leaving 101.7 g of a white solid, m.p. 155°–158° C. The filtrate is evaporated, filtered, the solid washed with ether and recrystallized from dioxane to give 7.8 g of additional white solid.

Step 3

6-(4-Chlorophenyl)-1-oxo-4-thio-1,2,3,4-tetrahydro-1,3,5-triazine

Aqueous sodium hydroxide (50%, 12.4 g) is added dropwise to a suspension of N-(4-chlorobenzoyl)-N'-carbamoyl thiourea (20.0 g) in $H_2O$ and the reaction mixture stirred for 90 min. The product is precipitated by the addition of glacial acetic acid, filtered and washed with distilled $H_2O$. The solid is suspended in refluxing ethanol, filtered and vacuum dried at 95° C. overnight, yielding 13.3 g of the triazine, m.p. 271°–274° C.

Step 4

6-(4-Chlorophenyl)-2-hydroxy-4-methylthio-1,3,5-triazine 82.40 g of the thio triazine, obtained in step 3 above, are suspended in methanol (1250 ml), to which is added a solution of sodium methoxide (19.0 g) in methanol (400 ml). Methyliodide (22 ml) in methanol (100 ml) is added to the reaction mixture dropwise followed by the formation of a precipitate. Mechanical stirring is continued 30 min after the addition is complete. The solid is filtered, washed with $H_2O$, air dried and recrystallized from THF yielding 52.10 g of the methylthio triazine as a creme colored solid.

Step 5

6-(4-Chlorophenyl)-2-hydroxy-4-methylhydrazine-1,3,5-triazine

A solution of methylhydrazine (3 ml) in ethanol (100 ml) is added dropwise to a suspension of 10.0 g of the methylthio triazine, obtained in step 4 above, dissolved in absolute ethanol (800 ml). The reaction mixture is heated to reflux and refluxed for 30 min, cooled and stirred overnight. Methylhydrazine (1 ml) is added to the reaction mixture which is again refluxed for 1.5 hours. The reaction mixture is cooled to RT, filtered, the solid washed with ether, suspended in 400 ml of boiling THF, filtered and the solid recrystallized from DMF to give 7.3 g of solid product, m.p. 250° C.

EXAMPLE IV

Preparation of
6-(4-Chlorophenyl)-4-hydrazino-2-hydroxy-1,3,5-triazine

A solution of hydrazine hydrate (3 ml) in methanol (100 ml) is added dropwise to a suspension of 6-(4-chlorophenyl)-2-hydroxy-4-methylthio-1,3,5-triazine (10.0 g) in methanol (700 ml). After addition is complete the reaction mixture is heated to reflux for 1.5 hour. The precipitate is filtered, washed with methanol and air dried to give 8.3 g of the hydrazinyl triazinone, m.p. 250° C.

EXAMPLE V

Preparation of
4-Acetylhydrazino-6-(4-Chlorophenyl)-2-hydroxy-1,3,5-triazine

Acetic anhydride (6 ml) is added to a suspension of 6-(4-chlorophenyl)-4-hydrazino-2-hydroxy-1,3,5-triazine in THF (500 ml) and the mixture stirred under reflux for 2½ hours. The mixture is cooled to RT overnight and the solid filtered, washed with ether and air dried, yielding 13.95 g of the solid. The solid is washed in 500 ml of boiling dioxane, filtered, washed with ether and air dried, leaving 13.8 g of the acetyl hydrazine triazine, m.p. 250° C.

EXAMPLE VI

Preparation of
4-Hydrazinyl-2-hydroxy-6-(4-pyridyl)-1,3,5-triazine dihydrochloride

Step 1

Ethyl isonicotinimidate

A solution of 4-cyanopyridine (135 g) and ethanol (83.3 ml) in chloroform (1000 ml) is cooled in an ice bath for 30 min. Anhydrous HCl (143 g) is bubbled into the cold mixture over a period of 7 hours with stirring continued overnight with cooling. The reaction mixture is filtered and the filtered solid added portionwise to an ice cold 10% $K_2CO_3$ solution (500 g in 5 l $H_2O$) with stirring. A liter of ether is added to the mixture after 20 min with stirring. The aqueous layer is extracted with ether and the organic extracts combined and dried overnight. The dried solution is filtered, evaporated in vacuo and vacuum distilled giving as a main fraction 75.5 g of a colorless liquid, b.p. 63°–65° C. (0.14 mm).

Step 2

Isonicotinamidine Hydrochloride

An aqueous solution of $NH_4Cl$ (26.9 g) is added to a solution of ethyl isonicotinimidate (75.5 g) in ethanol (325 ml). The reaction mixture is heated to reflux for four hours and stirred overnight. A white precipitate is filtered, washed with the mother liquor, dried at 90° C. under house vacuum for 8 hours, yielding 47 g of a white crystalline solid mp. 233°–237° C. The precipitate is dried overnight yielding 44.2 g of the desired hydrochloride, m.p. 237°–240° C.

Step 3

6-(4-pyridyl)-2-oxo-4-thio-1,4,5,6-tetrahydro-1,3,5-triazine

A solution of ethoxy carbonyl isothiocyanate (24.9 g) in 200 ml of toluene and a solution of 2 N NaOH (225 ml) are added simultaneously to a stirred solution of isonicotinamidine hydrochloride (23.64 g) in water (225 m) and toluene (700 ml) at RT. Stirring is continued overnight. The toluene layer is separated and extracted with 1 N NaOH solution. The combined aqueous portions are acidified with about 245 ml of 10% $H_2SO_4$ until the pH is about 1. A yellow precipitate forms which is collected, washed with water and dried at 70° C. under house vacuum over the weekend. The crude product is stirred with 850 ml of acetone for 2 hours, filtered, washed with acetone and dried at 90° C. under house vacuum for 4 hours yielding 25.5 g of a dark yellow solid m.p. 290° C.

Step 4

2-Hydroxy-4-methylthio-6-(4-pyridyl)-1,3,5-triazine

Sodium methylate (8.33 g) is added to a suspension of the thiotriazine (26.5 g), obtained in step 3 above, in methanol (428 ml). The mixture is stirred for 2.5 hours and methyl iodide (10 ml) added. Stirring is continued for 16 hours after which the mixture is filtered. The solid is washed with methanol, suspended in 500 ml of methanol and stirred at RT. The suspension is filtered, washed with methanol, dried at 90° C. under house vacuum for 4 hours yielding 27. g of the methylthiotriazine as a light yellow solid, m.p. 270°–271.5° C.

Step 5

4-Hydrazino-2-hydroxy-6-(4-pyridyl)-1,3,5-triazine dihydrochloride

Hydrazine hydrate (1.94 g) is added to a stirred solution of the methylthiotriazine (6.6 g), obtained in step 4 above, in 200 ml of methanol in a 472 ml Parr bomb. The bomb is sealed and stirred at RT for about 24 hours. The reaction mixture is filtered, washed with methanol and dried at 70° C. under house vacuum for 2 hours giving 4.9 g of a light yellow solid as the desired product, m.p. 300°–302° C. The yellow solid is stirred with HCl-methanol solution at room temperature for 2.5 hours. The suspension is filtered, the solid is stirred with methanol for 3 hours, filtered, washed with methanol and dried at 70° C. under house vacuum overnight yielding 5.4 g of the desired hydrazinyl triazinone dihydrochloride, mp. 257°–258° C.

The 4-hydrazino-2-hydroxy-1,3,5-triazines of Table II may be prepared from the corresponding 4-methoxy-2-hydroxy-1,3,5-triazines or 4-methylthio-2-hydroxy-1,3,5-triazines disclosed in Table I.

TABLE I 4-methoxy-6-benzyl-2-hydroxy-1,3,5-triazine
4-methoxy-6-(2-methylphenyl)-2-hydroxy-1,3,5-triazine
4-methoxy-6-(2-ethylphenyl)-2-hydroxy-1,3,5-triazine
4-methoxy-6-(2,6-dimethylphenyl)-2-hydroxy-1,3,5-triazine
4-methoxy-6-(2,6-diethylphenyl)-2-hydroxy-1,3,5-triazine
4-methoxy-6-(2-chlorophenyl)-2-hydroxy-1,3,5-triazine
4-methoxy-6-(3-chlorophenyl)-2-hydroxy-1,3,5-triazine
4-methoxy-6-(4-chlorophenyl)-2-hydroxy-1,3,5-triazine
4-methoxy-6-(2-chloro-6-bromophenyl)-2-hydroxy-1,3,5-triazine
4-methoxy-6-(3,4-dihydroxyphenyl)-2-hydroxy-1,3,5-triazine
4-methoxy-6-(3,4-dichlorophenyl)-2-hydroxy-1,3,5-triazine
4-methoxy-6-(3,4-dimethoxyphenyl)-2-hydroxy-1,3,5-triazine
4-methoxy-6-(3,5-dichlorophenyl)-2-hydroxy-1,3,5-triazine
4-methoxy-6-(3,4-diacetoxyphenyl)-2-hydroxy-1,3,5-triazine
4-methoxy-6-(3,4-diethoxyphenyl)-2-hydroxy-1,3,5-triazine
4-methoxy-6-(2-pyridyl)-2-hydroxy-1,3,5-triazine
4-methoxy-6-(3-pyridyl)-2-hydroxy-1,3,5-triazine
4-methoxy-6-(4-pyridyl)-2-hydroxy-1,3,5-triazine
4-methoxy-6-[2-(3-methylpyridyl)]-2-hydroxy-1,3,5-triazine
4-methoxy-6-[2-(4-methylpyridyl)]-2-hydroxy-1,3,5-triazine
4-methoxy-6-[2-(5-methylpyridyl)]-2-hydroxy-1,3,5-triazine
4-methoxy-6-[2-(3-chloropyridyl)]-2-hydroxy-1,3,5-triazine
4-methoxy-6-[2-(4-chloropyridyl)]-2-hydroxy-1,3,5-triazine
4-methoxy-6-[2-(3-carbomethoxypyridyl)]-2-hydroxy-1,3,5-triazine
4-methoxy-6-[2-(3-cyanopyridyl)]-2-hydroxy-1,3,5-triazine
4-methoxy-6-[2-(3-methoxypyridyl)]-2-hydroxy-1,3,5-triazine
4-methylthio-6-benzyl-2-hydroxy-1,3,5-triazine
4-methylthio-6-(2-methylphenyl)-2-hydroxy-1,3,5-triazine
4-methylthio-6-(2-ethylphenyl)-2-hydroxy-1,3,5-triazine
4-methylthio-6-(2,6-dimethylphenyl)-2-hydroxy-1,3,5-triazine
4-methylthio-6-(2,6-diethylphenyl)-2-hydroxy-1,3,5-triazine
4-methylthio-6-(2-chlorophenyl)-2-hydroxy-1,3,5-triazine
4-methylthio-6-(3-chlorophenyl)-2-hydroxy-1,3,5-triazine
4-methylthio-6-(4-chlorophenyl)-2-hydroxy-1,3,5-triazine
4-methylthio-6-(2-chloro-6-bromophenyl)-2-hydroxy-1,3,5-triazine
4-methylthio-6-(3,4-dihydroxyphenyl)-2-hydroxy-1,3,5-triazine
4-methylthio-6-(3,4-dichlorophenyl)-2-hydroxy-1,3,5-triazine
4-methylthio-6-(3,4-dimethoxyphenyl)-2-hydroxy-1,3,5-triazine
4-methylthio-6-(3,5-dichlorophenyl)-2-hydroxy-1,3,5-triazine
4-methylthio-6-(3,4-diacetoxyphenyl)-2-hydroxy-1,3,5-triazine
4-methylthio-6-(3,4-diethoxyphenyl)-2-hydroxy-1,3,5-triazine
4-methylthio-6-(2-pyridyl)-2-hydroxy-1,3,5-triazine
4-methylthio-6-(3-pyridyl)-2-hydroxy-1,3,5-triazine
4-methylthio-6-(4-pyridyl)-2-hydroxy-1,3,5-triazine
4-methylthio-6-[2-(3-methylpyridyl)]-2-hydroxy-1,3,5-triazine 4-methylthio-6-[2-(4-methylpyridyl)]-2-hydroxy-1,3,5-triazine
4-methylthio-6-[2-(5-methylpyridyl)]-2-hydroxy-1,3,5-triazine
4-methylthio-6-[2-(3-chloropyridyl)]-2-hydroxy-1,3,5-triazine
4-methylthio-6-[2-(4-chloropyridyl)]-2-hydroxy-1,3,5-triazine
4-methylthio-6-[2-(3-carbomethoxypyridyl)]-2-hydroxy-1,3,5-triazine
4-methylthio-6-[2-(3-cyanopyridyl)]-2-hydroxy-1,3,5-triazine
4-methylthio-6-[2-(3-methoxypyridyl]-2-hydroxy-1,3,5-triazine

TABLE II 4-hydrazino-6-benzyl-2-hydroxy-1,3,5-triazine
4-hydrazino-6-(2-methylphenyl)-2-hydroxy-1,3,5-triazine
4-hydrazino-6-(2-ethylphenyl)-2-hydroxy-1,3,5-triazine
4-hydrazino-6-(2,6-dimethylphenyl)-2-hydroxy-1,3,5-triazine
4-hydrazino-6-(2,6-diethylphenyl)-2-hydroxy-1,3,5-triazine
4-hydrazino-6-(2-chlorophenyl)-2-hydroxy-1,3,5-triazine
4-hydrazino-6-(3-chlorophenyl)-2-hydroxy-1,3,5-triazine
4-hydrazino-6-(4-chlorophenyl)-2-hydroxy-1,3,5-triazine
4-hydrazino-6-(2-chloro-6-bromophenyl)-2-hydroxy-1,3,5-triazine
4-hydrazino-6-(3,4-dihydroxyphenyl)-2-hydroxy-1,3,5-triazine
4-hydrazino-6-(3,4-dichlorophenyl)-2-hydroxy-1,3,5-triazine
4-hydrazino-6-(3,4-dimethoxyphenyl)-2-hydroxy-1,3,5-triazine
4-hydrazino-6-(3,5-dichlorophenyl)-2-hydroxy-1,3,5-triazine
4-hydrazino-6-(3,4-diacetoxyphenyl)-2-hydroxy-1,3,5-triazine
4-hydrazino-6-(3,4-diethoxyphenyl)-2-hydroxy-1,3,5-triazine
4-hydrazino-6-(2-pyridyl)-2-hydroxy-1,3,5-triazine
4-hydrazino-6-(3-pyridyl)-2-hydroxy-1,3,5-triazine
4-hydrazino-6-(4-pyridyl-2-hydroxy-1,3,5-triazine
4-hydrazino-6-[2-(3-methylpyridyl)]-2-hydroxy-1,3,5-triazine
4-hydrazino-6-[2-(4-methylpyridyl)]-2-hydroxy-1,3,5-triazine
4-hydrazino-6-[2-(5-methylpyridyl)]-2-hydroxy-1,3,5-triazine
4-hydrazino-6-[2-(3-chloropyridyl)]-2-hydroxy-1,3,5-triazine
4-hydrazino-6-[2-(4-chloropyridyl)]-2-hydroxy-1,3,5-triazine
4-hydrazino-6-[2-(3-carbomethoxypyridyl)]-2-hydroxy-1,3,5-triazine
4-hydrazino-6-[2-(3-cyanopyridyl)]-2-hydroxy-1,3,5-triazine
4-hydrazino-6-[2-(3-methoxypyridyl)]-2-hydroxy-1,e,5-triazine
4-methylhydrazino-6-benzyl-2-hydroxy-1,3,5-triazine
4-methylhydrazino-6-(2-methylphenyl)-2-hydroxy-1,3,5-triazine
4-methylhydrazino-6-(2-ethylphenyl)-2-hydroxy-1,3,5-triazine
4-methylhydrazino-6-(2,6-dimethylphenyl)-2-hydroxy-1,3,5-triazine
4-methylhydrazino-6-(2,6-diethylphenyl)-2-hydroxy-1,3,5-triazine
4-methylhydrazino-6-(2-chlorophenyl)-2-hydroxy-1,3,5-triazine
4-methylhydrazino-6-(3-chlorophenyl)-2-hydroxy-1,3,5-triazine
4-methylhydrazino-6-(4-chlorophenyl)-2-hydroxy-1,3,5-triazine
4-methylhydrazino-6-(2-chloro-6-bromophenyl)-2-hydroxy-1,3,5-triazine
4-methylhydrazino-6-(3,4-dihydroxyphenyl)-2-hydroxy-1,3,5-triazine
4-methylhydrazino-6-(3,4-dichlorophenyl)-2-hydroxy-1,3,5-triazine
4-methylhydrazino-6-(3,4-dimethoxyphenyl)-2-hydroxy-1,3,5-triazine
4-methylhydrazino-6-(3,5-dichlorophenyl)-2-hydroxy-1,3,5-triazine
4-methylhydrazino-6-(3,4-diacetoxyphenyl)-2-hydroxy-1,3,5-triazine
4-methylhydrazino-6-(3,4-diethoxyphenyl)-2-hydroxy-1,3,5-triazine
4-methylhydrazino-6-(2-pyridyl)-2-hydroxy-1,3,5-triazine
4-methylhydrazino-6-(3-pyridyl)-2-hydroxy-1,3,5-triazine
4-methylhydrazino-6-(4-pyridyl)-2-hydroxy-1,3,5-triazine
4-methylhydrazino-6-[2-(3-methylpyridyl)]-2-hydroxy-1,3,5-triazine
4-methylhydrazino-6-[2-(4-methylpyridyl)]-2-hydroxy-1,3,5-triazine
4-methylhydrazino-6-[2-(5-methylpyridyl)]-2-hydroxy-1,3,5-triazine
4-methylhydrazino-6-[2-(3-chloropyridyl)]-2-hydroxy-1,3,5-triazine
4-methylhydrazino-6-[2-(4-chloropyridyl)]-2-hydroxy-1,3,5-triazine
4-methylhydrazino-6-[2-chloro-6-bromophenyl)]-2-hydroxy-1,3,5-triazine
4-methylhydrazino-6-[2-(3-cyanopyridyl)]-2-hydroxy-1,3,5-triazine
4-methylhydrazino-6-[2-(3-methoxypyridyl)]-2-hydroxy-1,3,5-triazine
4-acetylhydrazino-6-benzyl-2-hydroxy-1,3,5-triazine
4-acetylhydrazino-6-(2-methylphenyl)-2-hydroxy-1,3,5-triazine
4-acetylhydrazino-6-(2-ethylphenyl)-2-hydroxy-1,3,5-triazine
4-acetylhydrazino-6-(2,6-dimethylphenyl)-2-hydroxy-1,3,5-triazine
4-acetylhydrazino-6-(2,6-diethylphenyl)-2-hydroxy-1,3,5-triazine
4-acetylhydrazino-6-(2-chlorophenyl)-2-hydroxy-1,3,5-triazine
4-acetylhydrazino-6-(3-chlorophenyl)-2-hydroxy-1,3,5-triazine
4-acetylhydrazino-6-(4-chlorophenyl)-2-hydroxy-1,3,5-triazine
4-acetylhydrazino-6-(2-chloro-6-bromophenyl)-2-hydroxy-1,3,5-triazine
4-acetylhydrazino-6-(3,4-dihydroxyphenyl)-2-hydroxy-1,3,5-triazine
4-acetylhydrazino-6-(3,4-dichlorophenyl)-2-hydroxy-1,3,5-triazine 4-acetylhydrazino-6-(3,4-dimethoxyphenyl)-2-hydroxy-1,3,5-triazine
4-acetylhydrazino-6-(3,5-dichlorophenyl)-2-hydroxy-1,3,5-triazine
4-acetylhydrazino-6-(3,4-diacetoxyphenyl)-2-hydroxy-1,3,5-triazine
4-acetylhydrazino-6-(3,4-diethoxyphenyl)-2-hydroxy-1,3,5-triazine
4-acetylhydrazino-6-(2-pyridyl)-2-hydroxy-1,3,5-triazine
4-acetylhydrazino-6-(3-pyridyl)-2-hydroxy-1,3,5-triazine
4-acetylhydrazino-6-(4-pyridyl)-2-hydroxy-1,3,5-triazine
4-acetylhydrazino-6-[2-(3-methylpyridyl)]-2-hydroxy-1,3,5-triazine
4-acetylhydrazino-6-[2-(4-methylpyridyl)]-2-hydroxy-1,3,5-triazine
4-acetylhydrazino-6-[2-(5-methylpyridyl)]-2-hydroxy-1,3,5-triazine
4-acetylhydrazino-6-[2-(3-chloropyridyl)]-2-hydroxy-1,3,5-triazine
4-acetylhydrazino-6-[2-(4-chloropyridyl)]-2-hydroxy-1,3,5-triazine
4-acetylhydrazino-6-[2-(3-carbomethoxypyridyl)]-2-hydroxy-1,3,5-triazine
4-acetylhydrazino-6-[2-(3-cyanopyridyl)]-2-hydroxy-1,3,5-triazine
4-acetylhydrazino-6-[2-(3-methoxypyridyl)]-2-hydroxy-1,3,5-triazine
4-trifluoromethylhydrazino-6-benzyl-2-hydroxy-1,3,5-triazine
4-trifluoromethylhydrazino-6-(2-methylphenyl)-2-hydroxy-1,3,5-triazine
4-trifluoromethylhydrazino-6-(2-ethylphenyl)-2-hydroxy-1,3,5-triazine
4-trifluoromethylhydrazino-6-(2,6-dimethylphenyl)-2-hydroxy-1,3,5-triazine
4-trifluoromethylhydrazino-6-(2,6-diethylphenyl)-2-hydroxy-1,3,5-triazine
4-trifluoromethylhydrazino-6-(2-chlorophenyl)-2-hydroxy-1,3,5-triazine
4-trifluoromethylhydrazino-6-(3-chlorophenyl)-2-hydroxy-1,3,5-triazine
4-trifluoromethylhydrazino-6-(4-chlorophenyl)-2-hydroxy-1,3,5-triazine
4-trifluoromethylhydrazino-6-(2-chloro-6-bromophenyl)-2-hydroxy-1,3,5-triazine
4-trifluoromethylhydrazino-6-(3,4-dihydroxyphenyl)-2-hydroxy-1,3,5-triazine
4-trifluoromethylhydrazino-6-(3,4-dichlorophenyl)-2-hydroxy-1,3,5-triazine
4-trifluoromethylhydrazine-6-(3,4-dimethoxyphenyl)-2-hydroxy-1,3,5-triazine
4-trifluoromethylhydrazino-6-(3,5-dichlorophenyl)-2-hydroxy-1,3,5-triazine
4-trifluoromethylhydrazino-6-(3,4-diacetoxyphenyl)-2-hydroxy-1,3,5-triazine
4-trifluoromethylhydrazino-6-(3,4-diethoxyphenyl)-2-hydroxy-1,3,5-triazine
4-trifluoromethylhydrazino-6-(2-pyridyl)-2-hydroxy-1,3,5-triazine
4-trifluoromethylhydrazino-6-(3-pyridyl)-2-hydroxy-1,3,5-triazine
4-trifluoromethylhydrazino-6-(4-pyridyl)-2-hydroxy-1,3,5-triazine
4-trifluoromethylhydrazino-6-[2-(3-methylpyridyl)]-2-hydroxy-1,3,5-triazine
4-trifluoromethylhydrazino-6-[2-(4-methylpyridyl)]-2-hydroxy-1,3,5-triazine
4-trifluoromethylhydrazino-6-[2-(5-methylpyridyl)]-2-hydroxy-1,3,5-triazine
4-trifluoromethylhydrazino-6-[2-(3-chloropyridyl)]-2-hydroxy-1,3,5-triazine
4-trifluoromethylhydrazino-6-[2-(4-chloropyridyl)]-2-hydroxy-1,3,5-triazine
4-trifluoromethylhydrazino-6-[2-(3-carbomethoxypyridyl)]-2-hydroxy-1,3,5-triazine
4-trifluoromethylhydrazine-6-[2-(3-cyanopyridyl)]-2-hydroxy-1,3,5-triazine
4-trifluoromethylhydrazino-6-[2-(3-methoxypyridyl)]-2-hydroxy-1,3,5-triazine
4-phenylhydrazino-6-benzyl-2-hydroxy-1,3,5-triazine
4-phenylhydrazino-6-(2-methylphenyl)-2-hydroxy-1,3,5-triazine
4-phenylhydrazino-6-(2-ethylphenyl)-2-hydroxy-1,3,5-triazine
4-phenylhydrazino-6-(2,6-dimethylphenyl)-2-hydroxy-1,3,5-triazine
4-phenylhydrazino-6-(2,6-diethylphenyl)-2-hydroxy-1,3,5-triazine
4-phenylhydrazino-6-(2-chlorophenyl)-2-hydroxy-1,3,5-triazine
4-phenylhydrazino-6-(3-chlorophenyl)-2-hydroxy-1,3,5-triazine
4-phenylhydrazino-6-(4-chlorophenyl)-2-hydroxy-1,3,5-triazine
4-phenylhydrazino-6-(2-chloro-6-bromophenyl)-2-hydroxy-1,3,5-triazine
4-phenylhydrazino-6-(3,4-dihydroxyphenyl)-2-hydroxy-1,3,5-triazine
4-phenylhydrazino-6-(3,4-dichlorophenyl)-2-hydroxy-1,3,5-triazine
4-phenylhydrazino-6-(3,4-dimethoxyphenyl)-2-hydroxy-1,3,5-triazine
4-phenylhydrazino-6-(3,5-dichlorophenyl)-2-hydroxy-1,3,5-triazine
4-phenylhydrazino-6-(3,4-diacetoxyphenyl)-2-hydroxy-1,3,5-triazine
4-phenylhydrazino-6-(3,4-diethoxyphenyl)-2-hydroxy-1,3,5-triazine
4-phenylhydrazino-6-(2-pyridyl)-2-hydroxy-1,3,5-triazine
4-phenylhydrazino-6-(3-pyridyl)-2-hydroxy-1,3,5-triazine
4-phenylhydrazino-6-(4-pyridyl)-2-hydroxy-1,3,5-triazine
4-phenylhydrazino-6-[2-(3-methylpyridyl)]-2-hydroxy-1,3,5-triazine
4-phenylhydrazino-6-[2-(4-methylpyridyl)]-2-hydroxy-1,3,5-triazine
4-phenylhydrazino-6-[2-(5-methylpyridyl)]-2-hydroxy-1,3,5-triazine
4-phenylhydrazino-6-[2-(3-chloropyridyl)]-2-hydroxy-1,3,5-triazine
4-phenylhydrazino-6-[2-(4-chloropyridyl)]-2-hydroxy-1,3,5-triazine
4-phenylhydrazino-6-[2-(3-carbomethoxypyridyl)]-2-hydroxy-1,3,5-triazine
4-phenylhydrazino-6-[2-(3-cyanopyridyl)]-2-hydroxy-1,3,5-triazine
4-phenylhydrazino-6-[2-(3-methoxypyridyl)]-2-hydroxy-1,3,5-triazine
4-benzylhydrazino-6-benzyl-2-hydroxy-1,3,5-triazine
4-benzylhydrazino-6-(2-methylphenyl)-2-hydroxy-1,3,5-triazine 4-benzylhydrazino-6-(2-ethylphenyl)-2-hydroxy-1,3,5-triazine
4-benzylhydrazino-6-(2,6-dimethylphenyl)-2-hydroxy-1,3,5-triazine
4-benzylhydrazino-6-(2,6-diethylphenyl)-2-hydroxy-1,3,5-triazine
4-benzylhydrazino-6-(2-chlorophenyl)-2-hydroxy-1,3,5-triazine
4-benzylhydrazino-6-(3-chlorophenyl)-2-hydroxy-1,3,5-triazine
4-benzylhydrazino-6-(4-chlorophenyl)-2-hydroxy-1,3,5-triazine
4-benzylhydrazino-6-(2-chloro-6-bromophenyl)-2-hydroxy-1,3,5-triazine
4-benzylhydrazino-6-(3,4-dihydroxyphenyl)-2-hydroxy-1,3,5-triazine
4-benzylhydrazino-6-(3,4-dichlorophenyl)-2-hydroxy-1,3,5-triazine
4-benzylhydrazino-6-(3,4-dimethoxyphenyl)-2-hydroxy-1,3,5-triazine
4-benzylhydrazino-6-(3,5-dichlorophenyl)-2-hydroxy-1,3,5-triazine
4-benzylhydrazino-6-(3,4-diacetoxyphenyl)-2-hydroxy-1,3,5-triazine
4-benzylhydrazino-6-(3,4-diethoxyphenyl)-2-hydroxy-1,3,5-triazine
4-benzylhydrazino-6-(2-pyridyl)-2-hydroxy-1,3,5-triazine
4-benzylhydrazino-6-(3-pyridyl)-2-hydroxy-1,3,5-triazine
4-benzylhydrazino-6-(4-pyridyl)-2-hydroxy-1,3,5-triazine
4-benzylhydrazino-6-[2-(3-methylpyridyl)]-2-hydroxy-1,3,5-triazine
4-benzylhydrazino-6-[2-(4-methylpyridyl)]-2-hydroxy-1,3,5-triazine
4-benzylhydrazino-6-[2-(5-methylpyridyl)]-2-hydroxy-1,3,5-triazine
4-benzylhydrazino-6-[2-(3-chloropyridyl)]-2-hydroxy-1,3,5-triazine
4-benzylhydrazino-6-[2-(4-chloropyridyl)]-2-hydroxy-1,3,5-triazine
4-benzylhydrazino-6-[2-(3-carbomethoxypyridyl)]-2-hydroxy-1,3,5-triazine
4-benzylhydrazino-6-[2-(3-cyanopyridyl)]-2-hydroxy-1,3,5-triazine
4-benzylhydrazino-6-[2-(3-methoxypyridyl)]-2-hydroxy-1,3,5-triazine
4-allylhydrazino-6-benzyl-2-hydroxy-1,3,5-triazine
4-allylhydrazino-6-(2-methylphenyl)-2-hydroxy-1,3,5-triazine
4-allylhydrazino-6-(2-ethylphenyl)-2-hydroxy-1,3,5-triazine
4-allylhydrazino-6-(2,6-dimethylphenyl)-2-hydroxy-1,3,5-triazine
4-allylhydrazino-6-(2,6-diethylphenyl)-2-hydroxy-1,3,5-triazine
4-allylhydrazino-6-(2-chlorophenyl)-2-hydroxy-1,3,5-triazine
4-allylhydrazino-6-(3-chlorophenyl)-2-hydroxy-1,3,5-triazine
4-allylhydrazino-6-(4-chlorophenyl)-2-hydroxy-1,3,5-triazine
4-allylhydrazino-6-(2-chloro-6-bromophenyl)-2-hydroxy-1,3,5-triazine
4-allylhydrazino-6-(3,4-dihydroxyphenyl)-2-hydroxy-1,3,5-triazine
4-allylhydrazino-6-(3,4-dichlorophenyl)-2-hydroxy-1,3,5-triazine
4-allylhydrazino-6-(3,4-dimethoxyphenyl)-2-hydroxy-1,3,5-triazine
4-allylhydrazino-6-(3,5-dichlorophenyl)-2-hydroxy-1,3,5-triazine
4-allylhydrazino-6-(3,4-diacetoxyphenyl)-2-hydroxy-1,3,5-triazine
4-allylhydrazino-6-(3,4-diethoxyphenyl)-2-hydroxy-1,3,5-triazine
4-allylhydrazino-6-(2-pyridyl)-2-hydroxy-1,3,5-triazine
4-allylhydrazino-6-(3-pyridyl)-2-hydroxy-1,3,5-triazine
4-allylhydrazino-6-(4-pyridyl)-2-hydroxy-1,3,5-triazine
4-allylhydrazino-6-[2-(3-methylpyridyl)]-2-hydroxy-1,3,5-triazine
4-allylhydrazino-6-[2-(4-methylpyridyl)]-2-hydroxy-1,3,5-triazine
4-allylhydrazino-6-[2-(5-methylpyridyl)]-2-hydroxy-1,3,5-triazine
4-allylhydrazino-6-[2-(3-chloropyridyl)]-2-hydroxy-1,3,5-triazine
4-allylhydrazino-6-[2-(4-chloropyridyl)]-2-hydroxy-1,3,5-triazine
4-allylhydrazino-6-[2-(3-carbomethoxypyridyl)]-2-hydroxy-1,3,5-triazine
4-allylhydrazino-6-[2-(3-cyanopyridyl)]-2-hydroxy-1,3,5-triazine
4-allylhydrazino-6-8 2-(3-methoxypyridyl)]-2-hydroxy-1,3,5-triazine The general synthesis described above may be utilized to prepare the 4-hydrazino-triazinones in Table III.

TABLE III 4-hydrazino-1-methyl-6-phenyl-1,2-dihydro-1,3,5-triazin-2-one
4-methylhydrazino-1-methyl-6-phenyl-1,2-dihydro-1,3,5-triazin-2-one
4-ethylhydrazino-1-methyl-6-phenyl-1,2-dihydro-1,3,5-triazin-2-one
4-propylhydrazino-1-methyl-6-phenyl-1,2-dihydro-1,3,5-triazin-2-one
4-phenylhydrazino-1-methyl-6-phenyl-1,2-dihydro-1,3,5-triazin-2-one
4-benzylhydrazino-1-methyl-6-phenyl-1,2-dihydro-1,3,5-triazin-2-one
4-allylhydrazino-1-methyl-6-phenyl-1,2-dihydro-1,3,5-triazin-2-one
4-propargylhydrazino-1-methyl-6-phenyl-1,2-dihydro-1,3,5-triazin-2-one
4-pyridylhydrazino-1-methyl-6-phenyl-1,2-dihydro-1,3,5-triazin-2-one
4-hydrazino-1-methyl-6-(2-methylphenyl)-1,2-dihydro-1,3,5-triazin-2-one
4-methylhydrazino-1-methyl-6-(2-methylphenyl)-1,2-dihydro-1,3,5-triazin-2-one
4-ethylhydrazino-1-methyl-6-(2-methylphenyl)-1,2-dihydro-1,3,5-triazin-2-one
4-propylhydrazino-1-methyl-6-(2-methylphenyl)-1,2-dihydro-1,3,5-triazin-2-one
4-phenylhydrazino-1-methyl-6-(2-methylphenyl)-1,2-dihydro-1,3,5-triazin-2-one
4-benzylhydrazino-1-methyl-6-(2-methylphenyl)-1,2-dihydro-1,3,5-triazin-2-one
4-allylhydrazino-1-methyl-6-(2-methylphenyl)-1,2-dihydro-1,3,5-triazin-2-one
4-propargylhydrazino-1-methyl-6-(2-methylphenyl)-1,2-dihydro-1,3,5-triazin-2-one 4-pyridylhydrazino-1-methyl-6-(2-methylphenyl)-1,2-dihydro-1,3,5-triazin-2-one
4-hydrazino-1-methyl-6-(2-ethylphenyl)-1,2-dihydro-1,3,5-triazin-2-one
4-methylhydrazino-1-methyl-6-(2-ethylphenyl)-1,2-dihydro-1,3,5-triazin-2-one
4-ethylhydrazino-1-methyl-6-(2-ethylphenyl)-1,2-dihydro-1,3,5-triazin-2-one
4-propylhydrazino-1-methyl-6-(2-ethylphenyl)-1,2-dihydro-1,3,5-triazin-2-one
4-phenylhydrazino-1-methyl-6-(2-ethylphenyl)-1,2-dihydro-1,3,5-triazin-2-one
4-benzylhydrazino-1-methyl-6-(2-ethylphenyl)-1,2-dihydro-1,3,5-triazin-2-one
4-allylhydrazino-1-methyl-6-(2-ethylphenyl)-1,2-dihydro-1,3,5-triazin-2-one
4-propargylhydrazino-1-methyl-6-(2-ethylphenyl)-1,2-dihydro-1,3,5-triazin-2-one
4-pyridylhydrazino-1-methyl-6-(2-ethylphenyl)-1,2-dihydro-1,3,5-triazin-2-one
4-hydrazino-1-methyl-6-(2-chlorophenyl)-1,2-dihydro-1,3,5-triazin-2-one
4-methylhydrazino-1-methyl-6-(2-chlorophenyl)-1,2-dihydro-1,3,5-triazin-2-one
4-ethylhydrazino-1-methyl-6-(2-chlorophenyl)-1,2-dihydro-1,3,5-triazin-2-one
4-propylhydrazino-1-methyl-6-(2-chlorophenyl)-1,2-dihydro-1,3,5-triazin-2-one
4-phenylhydrazino-1-methyl-6-(2-chlorophenyl)-1,2-dihydro-1,3,5-triazin-2-one
4-benzylhydrazino-1-methyl-6-(2-chlorophenyl)-1,2-dihydro-1,3,5-triazin-2-one
4-allylhydrazino-1-methyl-6-(2-chlorophenyl)-1,2-dihydro-1,3,5-triazin-2-one
4-propargylhydrazino-1-methyl-6-(2-chlorophenyl)-1,2-dihydro-1,3,5-triazin-2-one
4-pyridylhydrazino-1-methyl-6-(2-chlorophenyl)-1,2-dihydro-1,3,5-triazin-2-one
4-hydrazino-1-methyl-6-(3,4-dimethoxyphenyl)-1,2-dihydro-1,3,5-triazin-2-one
4-methylhydrazino-1-methyl-6-(3,4-dimethoxyphenyl)-1,2-dihydro-1,3,5-triazin-2-one
4-ethylhydrazino-1-methyl-6-(3,4-dimethoxyphenyl)-1,2-dihydro-1,3,5-triazin-2-one
4-propylhydrazino-1-methyl-6-(3,4-dimethoxyphenyl)-1,2-dihydro-1,3,5-triazin-2-one
4-phenylhydrazino-1-methyl-6-(3,4-dimethoxyphenyl)-1,2-dihydro-1,3,5-triazin-2-one
4-benzylhydrazino-1-methyl-6-(3,4-dimethoxyphenyl)-1,2-dihydro-1,3,5-triazin-2-one
4-allylhydrazino-1-methyl-6-(3,4-dimethoxyphenyl)-1,2-dihydro-1,3,5-triazin-2-one
4-propargylhydrazino-1-methyl-6-(3,4-dimethoxyphenyl)-1,2-dihydro-1,3,5-triazin-2-one
4-pyridylhydrazino-1-methyl-6-(3,4-dimethoxyphenyl)-1,2-dihydro-1,3,5-triazin-2-one
4-hydrazino-1-methyl-6-(3,4-dihydroxyphenyl)-1,2-dihydro-1,3,5-triazin-2-one
4-methylhydrazino-1-methyl-6-(3,4-dihydroxyphenyl)-1,2-dihydro-1,3,5-triazin-2-one
4-ethylhydrazino-1-methyl-6-(3,4-dihydroxyphenyl)-1,2-dihydro-1,3,5-triazin-2-one
4-propylhydrazino-1-methyl-6-(3,4-dihydroxyphenyl)-1,2-dihydro-1,3,5-triazin-2-one
4-phenylhydrazino-1-methyl-6-(3,4-dihydroxyphenyl)-1,2-dihydro-1,3,5-triazin-2-one
4-benzylhydrazino-1-methyl-6-(3,4-dihydroxyphenyl)-1,2-dihydro-1,3,5-triazin-2-one
4-allylhydrazino-1-methyl-6-(3,4-dihydroxyphenyl)-1,2-dihydro-1,3,5-triazin-2-one
4-propargylhydrazino-1-methyl-6-(3,4-dihydroxyphenyl)-1,2-dihydro-1,3,5-triazin-2-one
4-pyridylhydrazino-1-methyl-6-(3,4-dihydroxyphenyl)-1,2-dihydro-1,3,5-triazin-2-one
4-hydrazino-1-methyl-6-(3-chlorophenyl)-1,2-dihydro-1,3,5-triazin-2-one
4-methylhydrazino-1-methyl-6-(3-chlorophenyl)-1,2-dihydro-1,3,5-triazin-2-one
4-ethylhydrazino-1-methyl-6-(3-chlorophenyl)-1,2-dihydro-1,3,5-triazin-2-one
4-propylhydrazino-1-methyl-6-(3-chlorophenyl)-1,2-dihydro-1,3,5-triazin-2-one
4-phenylhydrazino-1-methyl-6-(3-chlorophenyl)-1,2-dihydro-1,3,5-triazin-2-one
4-benzylhydrazino-1-methyl-6-(3-chlorophenyl)-1,2-dihydro-1,3,5-triazin-2-one
4-allylhydrazino-1-methyl-6-(3-chlorophenyl)-1,2-dihydro-1,3,5-triazin-2-one
4-propargylhydrazino-1-methyl-6-(3-chlorophenyl)-1,2-dihydro-1,3,5-triazin-2-one
4-pyridylhydrazino-1-methyl-6-(3-chlorophenyl)-1,2-dihydro-1,3,5-triazin-2-one
4-hydrazino-1-methyl-6-(4-chlorophenyl)-1,2-dihydro-1,3,5-triazin-2-one
4-methylhydrazino-1-methyl-6-(4-chlorophenyl)-1,2-dihydro-1,3,5-triazin-2-one
4-ethylhydrazino-1-methyl-6-(4-chlorophenyl)-1,2-dihydro-1,3,5-triazin-2-one
4-propylhydrazino-1-methyl-6-(4-chlorophenyl)-1,2-dihydro-1,3,5-triazin-2-one
4-phenylhydrazino-1-methyl-6-(4-chlorophenyl)-1,2-dihydro-1,3,5-triazin-2-one
4-benzylhydrazino-1-methyl-6-(4-chlorophenyl)-1,2-dihydro-1,3,5-triazin-2-one
4-allylhydrazino-1-methyl-6-(4-chlorophenyl)-1,2-dihydro-1,3,5-triazin-2-one
4-propargylhydrazino-1-methyl-6-(4-chlorophenyl)-1,2-dihydro-1,3,5-triazin-2-one
4-pyridylhydrazino-1-methyl-6-(4-chlorophenyl)-1,2-dihydro-1,3,5-triazin-2-one
4-hydrazino-1-methyl-6-(3,4-dichlorophenyl)-1,2-dihydro-1,3,5-triazin-2-one
4-methylhydrazino-1-methyl-6-(3,4-dichlorophenyl)-1,2-dihydro-1,3,5-triazin-2-one
4-ethylhydrazino-1-methyl-6-(3,4-dichlorophenyl)-1,2-dihydro-1,3,5-triazin-2-one
4-propylhydrazino-1-methyl-6-(3,4-dichlorophenyl)-1,2-dihydro-1,3,5-triazin-2-one
4-phenylhydrazino-1-methyl-6-(3,4-dichlorophenyl)-1,2-dihydro-1,3,5-triazin-2-one
4-benzylhydrazino-1-methyl-6-(3,4-dichlorophenyl)-1,2-dihydro-1,3,5-triazin-2-one
4-allylhydrazino-1-methyl-6-(3,4-dichlorophenyl)-1,2-dihydro-1,3,5-triazin-2-one
4-propargylhydrazino-1-methyl-6-(3,4-dichlorophenyl)-1,2-dihydro-1,3,5-triazin-2-one
4-pyridylhydrazino-1-methyl-6-(3,4-dichlorophenyl)-1,2-dihydro-1,3,5-triazin-2-one
4-hydrazino-1-methyl-6-(2,6-diethylphenyl)-1,2-dihydro-1,3,5-triazin-2-one
4-methylhydrazino-1-methyl-6-(2,6-diethylphenyl)-1,2-dihydro-1,3,5-triazin-2-one
4-ethylhydrazino-1-methyl-6-(2,6-diethylphenyl)-1,2-dihydro-1,3,5-triazin-2-one
4-propylhydrazino-1-methyl-6-(2,6-diethylphenyl)-1,2-dihydro-1,3,5-triazin-2-one 4-phenylhydrazino-1-methyl-6-(2,6-diethylphenyl)-1,2-dihydro-1,3,5-triazin-2-one
4-benzylhydrazino-1-methyl-6-(2,6-diethylphenyl)-1,2-dihydro-1,3,5-triazin-2-one
4-allylhydrazino-1-methyl-6-(2,6-diethylphenyl)-1,2-dihydro-1,3,5-triazin-2-one
4-propargylhydrazino-1-methyl-6-(2,6-diethylphenyl)-1,2-dihydro-1,3,5-triazin-2-one
4-pyridylhydrazino-1-methyl-6-(2,6-diethylphenyl)-1,2-dihydro-1,3,5-triazin-2-one
4-hydrazino-1-methyl-6-(2,6-dichlorophenyl)-1,2-dihydro-1,3,5-triazin-2-one
4-methylhydrazino-1-methyl-6-(2,6-dichlorophenyl)-1,2-dihydro-1,3,5-triazin-2-one
4-ethylhydrazino-1-methyl-6-(2,6-dichlorophenyl)-1,2-dihydro-1,3,5-triazin-2-one
4-propylhydrazino-1-methyl-6-(2,6-dichlorophenyl)-1,2-dihydro-1,3,5-triazin-2-one
4-phenylhydrazino-1-methyl-6-(2,6-dichlorophenyl)-1,2-dihydro-1,3,5-triazin-2-one
4-benzylhydrazino-1-methyl-6-(2,6-dichlorophenyl)-1,2-dihydro-1,3,5-triazin-2-one
4-allylhydrazino-1-methyl-6-(2,6-dichlorophenyl)-1,2-dihydro-1,3,5-triazin-2-one
4-propargylhydrazino-1-methyl-6-(2,6-dichlorophenyl)-1,2-dihydro-1,3,5-triazin-2-one
4-pyridylhydrazino-1-methyl-6-(2,6-dichlorophenyl)-1,2-dihydro-1,3,5-triazin-2-one
4-hydrazino-1-ethyl-6-phenyl-1,2-dihydro-1,3,5-triazin-2-one
4-methylhydrazino-1-ethyl-6-phenyl-1,2-dihydro-1,3,5-triazin-2-one
4-ethylhydrazino-1-ethyl-6-phenyl-1,2-dihydro-1,3,5-triazin-2-one
4-propylhydrazino-1-ethyl-6-phenyl-1,2-dihydro-1,3,5-triazin-2-one
4-phenylhydrazino-1-ethyl-6-phenyl-1,2-dihydro-1,3,5-triazin-2-one
4-benzylhydrazino-1-ethyl-6-phenyl-1,2-dihydro-1,3,5-triazin-2-one
4-allylhydrazino-1-ethyl-6-phenyl-1,2-dihydro-1,3,5-triazin-2-one
4-propargylhydrazino-1-ethyl-6-phenyl-1,2-dihydro-1,3,5-triazin-2-one
4-pyridylhydrazino-1-ethyl-6-phenyl-1,2-dihydro-1,3,5-triazin-2-one
4-hydrazino-1-ethyl-6-(2-methylphenyl)-1,2-dihydro-1,3,5-triazin-2-one
4-methylhydrazino-1-ethyl-6-(2-methylphenyl)-1,2-dihydro-1,3,5-triazin-2-one
4-ethylhydrazino-1-ethyl-6-(2-methylphenyl)-1,2-dihydro-1,3,5-triazin-2-one
4-propylhydrazino-1-ethyl-6-(2-methylphenyl)-1,2-dihydro-1,3,5-triazin-2-one
4-phenylhydrazino-1-ethyl-6-(2-methylphenyl)-1,2-dihydro-1,3,5-triazin-2-one
4-benzylhydrazino-1-ethyl-6-(2-methylphenyl)-1,2-dihydro-1,3,5-triazin-2-one
4-allylhydrazino-1-ethyl-6-(2-methylphenyl)-1,2-dihydro-1,3,5-triazin-2-one
4-propargylhydrazino-1-ethyl-6-(2-methylphenyl)-1,2-dihydro-1,3,5-triazin-2-one
4-pyridylhydrazino-1-ethyl-6-(2-methylphenyl)-1,2-dihydro-1,3,5-triazin-2-one
4-hydrazino-1-ethyl-6-(2-ethylphenyl)-1,2-dihydro-1,3,5-triazin-2-one
4-methylhydrazino-1-ethyl-6-(2-ethylphenyl)-1,2-dihydro-1,3,5-triazin-2-one
4-ethylhydrazino-1-ethyl-6-(2-ethylphenyl)-1,2-dihydro-1,3,5-triazin-2-one
4-propylhydrazino-1-ethyl-6-(2-ethylphenyl)-1,2-dihydro-1,3,5-triazin-2-one
4-phenylhydrazino-1-ethyl-6-(2-ethylphenyl)-1,2-dihydro-1,3,5-triazin-2-one
4-benzylhydrazino-1-ethyl-6-(2-ethylphenyl)-1,2-dihydro-1,3,5-triazin-2-one
4-allylhydrazino-1-ethyl-6-(2-ethylphenyl)-1,2-dihydro-1,3,5-triazin-2-one
4-propargylhydrazino-1-ethyl-6-(2-ethylphenyl)-1,2-dihydro-1,3,5-triazin-2-one
4-pyridylhydrazino-1-ethyl-6-(2-ethylphenyl)-1,2-dihydro-1,3,5-triazin-2-one
4-hydrazino-1-ethyl-6-(2-chlorophenyl)-1,2-dihydro-1,3,5-triazin-2-one
4-methylhydrazino-1-ethyl-6-(2-chlorophenyl)-1,2-dihydro-1,3,5-triazin-2-one
4-ethylhydrazino-1-ethyl-6-(2-chlorophenyl)-1,2-dihydro-1,3,5-triazin-2-one
4-propylhydrazino-1-ethyl-6-(2-chlorophenyl)-1,2-dihydro-1,3,5-triazin-2-one
4-phenylhydrazino-1-ethyl-6-(2-chlorophenyl)-1,2-dihydro-1,3,5-triazin-2-one
4-benzylhydrazino-1-ethyl-6-(2-chlorophenyl)-1,2-dihydro-1,3,5-triazin-2-one
4-allylhydrazino-1-ethyl-6-(2-chlorophenyl)-1,2-dihydro-1,3,5-triazin-2-one
4-propargylhydrazino-1-ethyl-6-(2-chlorophenyl)-1,2-dihydro-1,3,5-triazin-2-one
4-pyridylhydrazino-1-ethyl-6-(2-chlorophenyl)-1,2-dihydro-1,3,5-triazin-2-one
4-hydrazino-1-ethyl-6-(4-chlorophenyl)-1,2-dihydro-1,3,5-triazin-2-one
4-methylhydrazino-1-ethyl-6-(4-chlorophenyl)-1,2-dihydro-1,3,5-triazino-2-one
4-ethylhydrazino-1-ethyl-6-(4-chlorophenyl)-1,2-dihydro-1,3,5-triazin-2-one
4-propylhydrazino-1-ethyl-6-(4-chlorophenyl)-1,2-dihydro-1,3,5-triazin-2-one
4-phenylhydrazino-1-ethyl-6-(4-chlorophenyl)-1,2-dihydro-1,3,5-triazin-2-one
4-benzylhydrazino-1-ethyl-6-(4-chlorophenyl)-1,2-dihydro-1,3,5-triazin-2-one
4-allylhydrazino-1-ethyl-6-(4-chlorophenyl)-1,2-dihydro-1,3,5-triazin-2-one
4-propargylhydrazino-1-ethyl-6-(4-chlorophenyl)-1,2-dihydro-1,3,5-triazin-2-one
4-pyridylhydrazino-1-ethyl-6-(4-chlorophenyl)-1,2-dihydro-1,3,5-triazin-2-one
4-hydrazino-1-ethyl-6-(3,4-dichlorophenyl)-1,2-dihydro-1,3,5-triazin-2-one
4-methylhydrazino-1-ethyl-6-(3,4-dichlorophenyl)-1,2-dihydro-1,3,5-triazin-2-one
4-ethylhydrazino-1-ethyl-6-(3,4-dichlorophenyl)-1,2-dihydro-1,3,5-triazin-2-one
4-propylhydrazino-1-ethyl-6-(3,4-dichlorophenyl)-1,2-dihydro-1,3,5-triazin-2-one
4-phenylhydrazino-1-ethyl-6-(3,4-dichlorophenyl)-1,2-dihydro-1,3,5-triazin-2-one
4-benzylhydrazino-1-ethyl-6-(3,4-dichlorophenyl)-1,2-dihydro-1,3,5-triazin-2-one
4-allylhydrazino-1-ethyl-6-(3,4-dichlorophenyl)-1,2-dihydro-1,3,5-triazin-2-one
4-propargylhydrazino-1-ethyl-6-(3,4-dichlorophenyl)-1,2-dihydro-1,3,5-triazin-2-one
4-pyridylhydrazino-1-ethyl-6-(3,4-dichlorophenyl)-1,2-dihydro-1,3,5-triazin-2-one 4-propargylhydrazino-1-ethyl-6-phenyl-1,2-dihydro-1,3,5-triazin-2-one
4-pyridylhydrazino-1-ethyl-6-phenyl-1,2-dihydro-1,3,5-triazin-2-one
4-hydrazino-1-ethyl-6-(3-chlorophenyl)-1,2-dihydro-1,3,5-triazin-2-one
4-methylhydrazino-1-ethyl-6-(3-chlorophenyl)-1,2-dihydro-1,3,5-triazin-2-one
4-ethylhydrazino-1-ethyl-6-(3-chlorophenyl)-1,2-dihydro-1,3,5-triazin-2-one
4-propylhydrazino-1-ethyl-6-(3-chlorophenyl)-1,2-dihydro-1,3,5-triazin-2-one
4-phenylhydrazino-1-ethyl-6-(3-chlorophenyl)-1,2-dihydro-1,3,5-triazin-2-one
4-benzylhydrazino-1-ethyl-6-(3-chlorophenyl)-1,2-dihydro-1,3,5-triazin-2-one
4-allylhydrazino-1-ethyl-6-(3-chlorophenyl)-1,2-dihydro-1,3,5-triazin-5-one
4-propargylhydrazino-1-ethyl-6-(3-chlorophenyl)-1,2-dihydro-1,3,5-triazin-2-one
4-pyridylhydrazino-1-ethyl-6-(3-chlorophenyl)-1,2-dihydro-1,3,5-triazin-2-one
4-hydrazino-1-ethyl-6-(3,4-ditrifluoroacetoxyphenyl)-1,2-dihydro-1,3,5-triazin-2-one
4-methylhydrazino-1-ethyl-6-(3,4-ditrifluoroacetoxyphenyl)-1,2-dihydro-1,3,5-triazin-2-one
4-ethylhydrazino-1-ethyl-6-(3,4-ditrifluoroacetoxyphenyl)-1,2-dihydro-1,3,5-triazin-2-one
4-propylhydrazino-1-ethyl-6-(3,4-ditrifluoroacetoxyphenyl)-1,2-dihydro-1,3,5-triazin-2-one
4-phenylhydrazino-1-ethyl-6-(3,4-ditrifluoroacetoxyphenyl)-1,2-dihydro-1,3,5-triazin-2-one
4-benzylhydrazino-1-ethyl-6-(3,4-ditrifluoroacetoxyphenyl)-1,2-dihydro-1,3,5-triazin-2-one
4-allylhydrazino-1-ethyl-6-(3,4-ditrifluoroacetoxyphenyl)-1,2-dihydro-1,3,5-triazin-2-one
4-propargylhydrazino-1-ethyl-6-(3,4-ditrifluoroacetoxyphenyl)-1,2-dihydro-1,3,5-triazin-2-one
4-pyridylhydrazino-1-ethyl-6-(3,4-ditrifluoroacetoxyphenyl)-1,2-dihydro-1,3,5-triazin-2-one
4-hydrazino-1-ethyl-6-(2,6-dimethylphenyl)-1,2-dihydro-1,3,5-triazin-2-one
4-methylhydrazino-1-ethyl-6-(2,6-dimethylphenyl)-1,2-dihydro-1,3,5-triazin-2-one
4-ethylhydrazino-1-ethyl-6-(2,6-dimethylphenyl)-1,2-dihydro-1,3,5-triazin-2-one
4-propylhydrazino-1-ethyl-6-(2,6-dimethylphenyl)-1,2-dihydro-1,3,5-triazin-2-one
4-phenylhydrazino-1-ethyl-6-(2-dimethylphenyl)-1,2-dihydro-1,3,5-triazin-2-one
4-benzylhydrazino-1-ethyl-6-(2,6-dimethylphenyl)-1,2-dihydro-1,3,5-triazin-2-one
4-allylhydrazino-1-ethyl-6-(2,6-dimethylphenyl)-1,2-dihydro-1,3,5-triazin-2-one
4-propargylhydrazino-1-ethyl-6-(2,6-dimethylphenyl)-1,2-dihydro-1,3,5-triazin-2-one
4-pyridylhydrazino-1-ethyl-6-(2,6-dimethylphenyl)-1,2-dihydro-1,3,5-triazin-2-one
4-hydrazino-1-ethyl-6-(2,6-diethylphenyl)-1,2-dihydro-1,3,5-triazin-2-one
4-methylhydrazino-1-ethyl-6-(2,6-diethylphenyl)-1,2-dihydro-1,3,5-triazin-2-one
4-ethylhydrazino-1-ethyl-6-(2,6-diethylphenyl)-1,2-dihydro-1,3,5-triazin-2-one
4-propylhydrazino-1-ethyl-6-(2,6-diethylphenyl)-1,2-dihydro-1,3,5-triazin-2-one
4-phenylhydrazino-1-ethyl-6-(2,6-diethylphenyl)-1,2-dihydro-1,3,5-triazin-2-one
4-benzylhydrazino-1-ethyl-6-(2,6-diethylphenyl)-1,2-dihydro-1,3,5-triazin-2-one
4-allylhydrazino-1-ethyl-6-(2,6-diethylphenyl)-1,2-dihydro-1,3,5-triazin-2-one
4-propargylhydrazino-1-ethyl-6-(2,6-diethylphenyl)-1,2-dihydro-1,3,5-triazin-2-one
4-pyridylhydrazino-1-ethyl-6-(2,6-diethylphenyl)-1,2-dihydro-1,3,5-triazin-2-one
4-hydrazino-1-ethyl-6-(2,6-dichlorophenyl)-1,2-dihydro-1,3,5-triazin-2-one
4-methylhydrazino-1-ethyl-6-(2,6-dichlorophenyl)-1,2-dihydro-1,3,5-triazin-2-one
4-ethylhydrazino-1-ethyl-6-(2,6-dichlorophenyl)-1,2-dihydro-1,3,5-triazin-2-one
4-propylhydrazino-1-ethyl-6-(2,6-dichlorophenyl)-1,2-dihydro-1,3,5-triazin-2-one
4-phenylhydrazino-1-ethyl-6-(2,6-dichlorophenyl)-1,2-dihydro-1,3,5-triazin-2-one
4-benzylhydrazino-1-ethyl-6-(2,6-dichlorophenyl)-1,2-dihydro-1,3,5-triazin-2-one
4-allylhydrazino-1-ethyl-6-(2,6-dichlorophenyl)-1,2-dihydro-1,3,5-triazin-2-one
4-propargylhydrazino-1-ethyl-6-(2,6-dichlorophenyl)-1,2-dihydro-1,3,5-triazin-2-one
4-pyridylhydrazino-1-ethyl-6-(2,6-dichlorophenyl)-1,2-dihydro-1,3,5-triazin-2-one Physical data on a representative number of 4-hydrazinyl-1,3,5-triazines is shown in Table IV.

TABLE IV

| | M.P. |
|---|---|
| 1-methyl-4-methylhydrazino-6-phenyl-1,2-dihydro-1,3,5-triazin-2-one hydrochloride | 127–129° |
| 4-acetylhydrazino-1-methyl-6-phenyl-1,2-dihydro-1,3,5-triazin-2-one | 228–229° C. |
| 4-hydrazino-1-methyl-6-phenyl-1,2-dihydro-1,3,5-triazin-2-one | 198–199° C. |
| 4-ethoxycarbonylhydrazino-1-methyl-6-phenyl-1,2-dihydro-1,3,5-triazin-2-one | 217.5° C. |
| 2-hydrazino-4-hydroxy-6-(4-pyridyl)-1,3,5-triazine dihydrochloride | 257–258° C. |
| 6-(4-chlorophenyl)-4-hydrazino-2-hydroxy-1,3,5-triazine | 250° C. 43 |
| 6-(4-chlorophenyl)-2-hydroxy-4-methylhydrazino-1,3,5-triazine | 250° C. |
| 6-(3-chlorophenyl)-2-hydroxy-4-methylhydrazino-1,3,5-triazine | 245–248° C. |
| 6-(3-chlorophenyl)-4-hydrazino-2-hydroxy-1,3,5-triazine | 250° C. |
| 4-acetylhydrazino-6-(3-chlorophenyl)-2-hydroxy-1,3,5-triazine | 250° C. |
| 2-hydroxy-4-methylhydrazino-6-(3-trifluoromethylphenyl)-1,3,5-triazine | 250° C. |
| 4-hydrazino-2-hydroxy-6-(3-trifluoromethylphenyl)-1,3,5-triazine | 250° C. |

The hydrazinyl compounds of this invention possess blood-pressure-lowering activity and are useful as antihypertensive agents.

For these purposes, the hydrazino triazinones (thiones) of this invention can be normally administered orally, parenterally or rectally. Orally they may be administered as tablets, aqueous or oily suspensions, dispersible powders or granules, emulsions, hard or soft capsules, or syrups or elixirs. Parenterally they may be administered as a salt in solution which pH is adjusted to physiologically accepted values. Aqueous solutions are preferred.

Compositions intended for oral use may be prepared according to any method known to the art for the manufacture of pharmaceutical compositions, and such compositions may contain one or more inert carrier agents selected from the group consisting of sweetening agents, flavoring agents, coloring agents, preserving agents and the like, in order to provide a pharmaceutically elegant and palatable preparation.

The dosage regimen in carrying out the methods of this invention is that which ensures maximum therapeutic response until improvement is obtained, and thereafter the minimum effective level which gives relief. Thus, in general, the dosages are those that are therapeutically effective in the alleviation of hypertensive disorders. The therapeutically effective doses correspond to those dosage amounts found effective in tests using animal models which are known to correlate to human activity. In general, it is expected that daily doses between about 5 mg/kg and about 300 mg/kg (preferably in the range of about 10 to about 50 mg/kg/day), will be sufficient to produce the desired therapeutic effect, bearing in mind, of course, that in selecting the appropriate dosage in any specific case, consideration must be give to the patient's weight, general health, age, the severity of the disorder, and other factors which may influence response to the drug.

Various tests in animals have been carried out to show the ability of the compounds of this invention to exhibit reactions that can be correlated with activity in humans. These tests involve such factors as their blood-pressure-lowering effect and determination of their toxicity. It has been found that the compounds of this invention, when tested in the above situation, show a marked activity.

Determination of Antihypertensive Activity

A description of the test protocol used in the determination of the antihypertensive activity of the compounds of this invention follows:

(a) Male TAC spontaneously hypertensive rats (SHR's), eleven weeks old, weighing 200–220 grams, are chosen for testing. The average systolic blood pressure (as measured below) should be 165 mmHg or above. Any rat not initially meeting this criterion is not utilized.

(b) A Beckman dynograph is balanced and calibrated using a Beckman indirect blood pressure coupler. A mercury monometer is placed on one arm of the glass "T" tube. The known pressure head in the tail cuff is synchronized with the recorder output so that 1 mm pen deflection=5 mmHg. Any correction is made using the chart calibration screw on the pressure coupler. The pulse amplitude is controlled by the pre-amplifier using a 20 v/cm setting.

The rats are prewarmed in groups of five for twenty minutes to dilate the tail artery from which the arterial pulse is recorded. After prewarming, each rat is placed in an individual restraining cage with continued warming. When the enclosure temperature has been maintained at 35° C. for 5 minutes, recordings are started. The tail cuff is placed on the rat's tail and the rubber bulb of the pneumatic tail cuff transducer is taped securely to the dorsal surface of the tail. When the rat's pulse reaches maximum amplitude and is unwavering, the cuff is inflated and the air slowly released. A reading of systolic blood pressure is read at the point of the chart when the first deflection appears on the chart recording while the air in the cuff is being released. The exact point of the systolic blood pressure reading is where the first deflection forms a 90° angle to the falling cuff pressure base line. After obtaining nine or ten consistent readings, the average of the middle five readings is calculated.

(c) Three groups of twenty rats receive the test composed at doses of about 25 mg/kg per os.

A fourth group of twenty control rats receive distilled water. Statistical comparisons of systolic pressure (four hours after the first dose and sixteen hours after the second dose) are made on a daily basis using the Student t test for dependent variables (see, E. Lord, *Biometrika*, 34, 56 (1947)), with the predose observations serving as baseline values for each rat.

This testing method is known to correlate well with antihypertensive activity in humans and is a standard test used to determine antihypertensive properties. In view of the results of this test, the hydrazino triazinones of this invention can be considered to be active antihypertensive agents.

We claim:

1. A compound of the formula

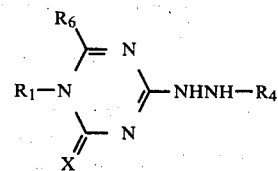

wherein:
X is oxygen or sulfur;
$R_1$ is hydrogen, lower alkyl, cycloalkyl of C3 to C6, lower alkenyl, lower alkynyl, phenyl loweralkyl or substituted phenyl loweralkyl;
$R_4$ is hydrogen, lower alkyl, cycloalkyl of C3 to C6, lower alkenyl, lower alkynyl, lower alkanoyl, carboloweralkoxy, carbamoyl, phenyl, substituted phenyl, benzoyl, substituted benzoyl, phenyl loweralkyl, substituted phenyl loweralkyl, heterocyclic, substituted heterocyclic, halo lower alkyl, or halo lower alkanoyl;
$R_6$ is phenyl, substituted phenyl, phenyl loweralkyl, substituted phenyl loweralkyl, heterocyclic, substituted heterocyclic, heterocyclic lower alkyl, or substituted heterocyclic lower alkyl;
wherein:
substituted phenyl means a phenyl group in which one or more of the phenyl hydrogens has been replaced by the same or different substituents selected from the group consisting of halo, lower alkyl, halo lower alkyl, nitro, amino, acylamino, hydroxy, lower alkoxy, phenyl lower alkoxy, acyloxy, cyano, halo lower alkoxy or lower alkyl sulfonyl;
wherein:
heterocyclic means a cyclic or bicyclic group having 1 to 3 hetero atoms which may be nitrogen, oxygen or sulfur, selected from the group consisting of oxazolidinyl, thiazolidinyl, pyrazolidinyl, imidazolidinyl, piperidyl, piperazinyl, thiamorpholinyl, 1-pyrrole, 2-pyrrole, 3-pyrrole, 2-furan, 3-furan, 2-thiophene, 3-thiophene, 2-tetrahydrothiophene, 3-tetrahydrothiophene, 1-imidazole, 2-imidazole, 4-imidazole, 5-imidazole, 2-oxazole, 4-oxazole, 5-oxazole, 2-thiazole, 4-thiazole, 5-thiazole, 1-pyrazole, 3-pyrazole, 4-pyrazole, 5-pyrazole, 1-pyrrolidine, 2-pyrrolidine, 3-pyrrolidine, 2-pyridyl, 3-pyridyl, 4-pyridyl, 2-pyrimidine, 4-pyrimidine, 5-pyrimidine, 6-pyrimidine, 2-purine, 6-purine, 8-purine, 9-purine, 2-quinoline, 3-quinoline, 4-quinoline, 5-quinoline, 6-quinoline, 7-quinoline, 8-quinoline, 1-isoquinoline, 3-isoquinoline, 4-isoquinoline, 5-isoquinoline, 6-isoquinoline, 7-isoquinoline, 8-isoquinoline, carbazole, trimethylenetriaminyl, ethyleneiminyl and morpholinyl; and wherein:

substituted heterocyclic means a heterocyclic group in which one or more of the hydrogens on the ring carbons have been replaced by substituents as given above with respect to substituted phenyl;

or a pharmaceutically acceptable acid addition salt thereof.

2. A compound of the formula

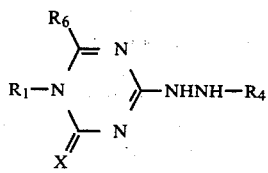

wherein:
X is oxygen or sulfur;
$R_1$ is hydrogen or lower alkyl;
$R_4$ is hydrogen, lower alkyl, cycloalkyl of C3 to C6, lower alkenyl, lower alkynyl, lower alkanoyl, carboloweralkoxy, carbamoyl, phenyl, substituted phenyl, benzoyl, substituted benzoyl, phenyl loweralkyl, substituted phenyl loweralkyl, heterocyclic, substituted heterocyclic, halo lower alkyl, or halo lower alkanoyl;
$R_6$ is phenyl, substituted phenyl, heterocyclic, substituted heterocyclic, heterocyclic lower alkyl or substituted heterocyclic lower alkyl;
wherein:
substituted phenyl means a phenyl group in which one or more of the phenyl hydrogens has been replaced by the same or different substituents including selected from the group consisting of halo, lower alkyl, halo lower alkyl, nitro, amino, acylamino, hydroxy, lower alkoxy, phenyl lower alkoxy, acyloxy, cyano, halo lower alkoxy or lower alkyl sulfonyl;
wherein:
heterocyclic means a cyclic or bicyclic group having 1 to 3 hetero atoms which may be nitrogen, oxygen or sulfur, selected from the group consisting of oxazolidinyl, thiazolidinyl, pyrazolidinyl, imidazolidinyl, piperidyl, piperazinyl, thiamorpholinyl, 1-pyrrole, 2-pyrrole, 3-pyrrole, 2-furan, 3-furan, 2-thiophene, 3-thiophene, 2-tetrahydrothiophene, 3-tetrahydrothiophene, 1-imidazole, 2-imidazole, 4-imidazole, 5-imidazole, 2-oxazole, 4-oxazole, 5-oxazole, 2-thiazole, 4-thiazole, 5-thiazole, 1-pyrazole, 3-pyrazole, 4-pyrazole, 5-pyrazole, 1-pyrrolidine, 2-pyrrolidine, 3-pyrrolidine, 2-pyridyl, 3-pyridyl, 4-pyridyl, 2-pyrimidine, 4-pyrimidine, 5-pyrimidine, 6-pyrimidine, 2-purine, 6-purine, 8-purine, 9-purine, 2-quinoline, 3-quinoline, 4-quinoline, 5-quinoline, 6-quinoline, 7-quinoline, 8-quinoline, 1-isoquinoline, 3-isoquinoline, 4-isoquinoline, 5-isoquinoline, 6-isoquinoline, 7-isoquinoline, 8-isoquinoline, carbazole, trimethylenetriaminyl, ethyleneiminyl and morpholinyl; and wherein:
substituted heterocyclic means a heterocyclic group in which one or more of the hydrogens on the ring carbons have been replaced by substituents as given above with respect to substituted phenyl;

or a pharmaceutically acceptable acid addition salt thereof.

3. A compound of the formula

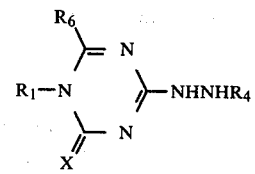

wherein:
X is oxygen or sulfur;
$R_1$ is hydrogen or lower alkyl;
$R_4$ is hydrogen, lower alkyl, lower alkanoyl, or halo lower alkanoyl;
$R_6$ is phenyl or substituted phenyl;
wherein:
substituted phenyl means phenyl in which one or more of the phenyl hydrogens has been replaced by the same or different substituents selected from the group consisting of halo, lower alkoxy, lower alkyl, halo lower alkyl, nitro, amino, lower alkanoyl, hydroxy, carbo lower alkoxy, phenyl lower alkoxy, lower alkylacyloxy, cyano, halo lower alkoxy and lower alkyl sulfonyl;

or a pharmaceutically acceptable acid addition salt thereof.

4. A compound according to any one of claims 1 to 3 wherein X is oxygen.

5. A compound according to any one of claims 1 to 3 wherein X is sulfur.

6. A compound of the formula

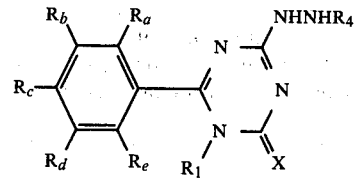

wherein:
X is oxygen or sulfur;
$R_1$ is hydrogen or lower alkyl;
$R_4$ is hydrogen, lower alkyl, lower alkanoyl, carboloweralkoxy, phenyl, benzoyl, substituted phenyl, pyridyl, or substituted pyridyl;
$R_a$, $R_b$, $R_c$, $R_d$ and $R_e$ are hydrogen, lower alkyl, lower alkoxy, halo, halo lower alkyl, amino, nitro, lower alkanoyl, lower alkyl, carbamoyl, hydroxy, cyano, carboloweralkoxy, carboxyl, or lower alkyl sulfonyl;
wherein:
substituted phenyl means a phenyl group in which one or more of the phenyl hydrogens has been replaced by the same or different substituents selected from the group consisting of halo, lower alkyl, halo lower alkyl, nitro, amino, acylamino, hydroxy, lower alkoxy, phenyl lower alkoxy, acyloxy, cyano, halo lower alkoxy or lower alkyl sulfonyl;
and wherein:

substituted pyridyl means a pyridyl group in which one or more of the hydrogens on pyridyl ring carbons have been replaced by substituents as given above with respect to substituted phenyl;
or a pharmaceutically acceptable acid addition salt thereof.

7. A compound according to claim 6 wherein:
$R_1$ is hydrogen or lower alkyl; and
$R_a$, $R_b$, $R_c$, $R_d$ and $R_e$ are hydrogen; or a pharmaceutically acceptable acid addition salt thereof.

8. A compound according to claim 6 wherein:
$R_1$ is hydrogen or lower alkyl;
$R_a$, $R_b$, $R_c$, $R_d$ and $R_e$ are hydrogen, lower alkyl, halo, lower alkoxy, nitro, or halo lower alkyl, provided that at least one of $R_a$, $R_b$, $R_c$ and $R_d$ is other than hydrogen;
or a pharmaceutically acceptable acid addition salt thereof.

9. A compound according to claim 6 wherein:
$R_1$ is hydrogen or lower alkyl;
$R_a$ and $R_e$ are hydrogen;
$R_b$, $R_c$ and $R_d$ are hydrogen, lower alkoxy, halo, nitro, and halo lower alkyl; provided that at least one of $R_b$, $R_c$ and $R_d$ is other than hydrogen;
or a pharmaceutically acceptable acid addition salt thereof.

10. A compound according to the formula

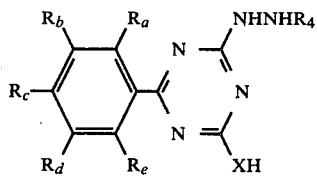

wherein:
X is oxygen or sulfur;
$R_4$ is hydrogen, methyl or acetyl;
$R_a$, $R_b$, $R_c$, $R_d$ and $R_e$ are hydrogen, halo or alkyl;
or a pharmaceutically acceptable acid addition salt thereof.

11. A compound according to the formula

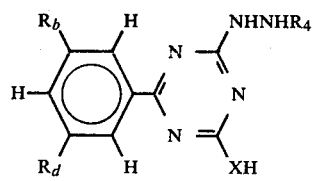

wherein:
X is oxygen or sulfur;
$R_4$ is hydrogen, lower alkyl, or lower alkanoyl;
$R_b$ and $R_d$ are hydrogen or halo; provided that at least one of $R_b$ and $R_d$ is halo;
or a pharmaceutically acceptable acid addition salt thereof.

12. A compound according to claim 6, 10 or 11 wherein X is oxygen.

13. A compound according to claim 6, 10 or 11 wherein X is sulfur.

14. A method for lowering blood pressure in humans and other mammals which comprises administering thereto an effective blood pressure lowering amount of a compound of the formula

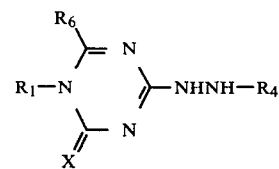

wherein:
X is oxygen or sulfur;
$R_1$ is hydrogen, lower alkyl, cycloalkyl of C3 to C6, lower alkenyl, lower alkynyl, phenyl loweralkyl or substituted phenyl loweralkyl;
$R_4$ is hydrogen, lower alkyl, cycloalkyl of C3 to C6, lower alkenyl, lower alkynyl, lower alkanoyl, carboloweralkoxy, carbamoyl, phenyl, substituted phenyl, benzoyl, substituted benzoyl, phenyl loweralkyl, substituted phenyl loweralkyl, heterocyclic, substituted heterocyclic, halo lower alkyl, or halo lower alkanoyl;
$R_6$ is phenyl, substituted phenyl, phenyl loweralkyl, substituted phenyl loweralkyl, heterocyclic, substituted heterocyclic, heterocyclic lower alkyl, or substituted heterocyclic lower alkyl;
wherein:
substituted phenyl means a phenyl group in which one or more of the phenyl hydrogens has been replaced by the same or different substituents selected from the group consisting of halo, lower alkyl, halo lower alkyl, nitro, amino, acylamino, hydroxy, lower alkoxy, phenyl lower alkoxy, acyloxy, cyano, halo lower alkoxy or lower alkyl sulfonyl;
wherein:
heterocyclic means a cyclic or bicyclic group having 1 to 3 hetero atoms which may be nitrogen, oxygen or sulfur, selected from the group consisting of oxazolidinyl, thiazolidinyl, pyrazolidinyl, imidazolidinyl, piperidyl, piperazinyl, thiamorpholinyl, 1-pyrrole, 2-pyrrole, 3-pyrrole, 2-furan, 3-furan, 2-thiophene, 3-thiophene, 2-tetrahydrothiophene, 3-tetrahydrothiophene, 1-imidazole, 2-imidazole, 4-imidazole, 5-imidazole, 2-oxazole, 4-oxazole, 5-oxazole, 2-thiazole, 4-thiazole, 5-thiazole, 1-pyrazole, 3-pyrazole, 4-pyrazole, 5-pyrazole, 1-pyrrolidine, 2-pyrrolidine, 3-pyrrolidine, 2-pyridyl, 3-pyridyl, 4-pyridyl, 2-pyrimidine, 4-pyrimidine, 5-pyrimidine, 6-pyrimidine, 2-purine, 6-purine, 8-purine, 9-purine, 2-quinoline, 3-quinoline, 4-quinoline, 5-quinoline, 6-quinoline, 7-quinoline, 8-quinoline, 1-isoquinoline, 3-isoquinoline, 4-isoquinoline, 5-isoquinoline, 6-isoquinoline, 7-isoquinoline, 8-isoquinoline, carbazole, trimethylenetriaminyl, ethyleneiminyl and morpholinyl;
and wherein:
substituted heterocyclic means a heterocyclic group in which one or more of the hydrogens on the ring carbons have been replaced by substituents as given above with respect to substituted phenyl;
or a pharmaceutically acceptable acid addition salt thereof.

15. A method for lowering blood pressure in humans and other mammals which comprises administering thereto an effective blood pressure lowering amount of a compound of the formula

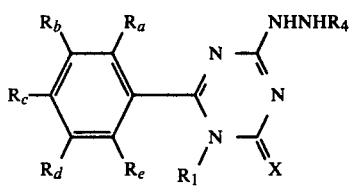

wherein:
X is oxygen or sulfur;
R₁ is hydrogen or lower alkyl;
R₄ is hydrogen, lower alkyl, lower alkanoyl, carboloweralkoxy, phenyl, benzoyl, substituted phenyl, pyridyl, or substituted pyridyl;
R$_a$, R$_b$, R$_c$, R$_d$ and R$_e$ are hydrogen, lower alkyl, lower alkoxy, halo, halo lower alkyl, amino, nitro, lower alkanoyl, lower alkyl, carbamoyl, hydroxy, cyano, carboloweralkoxy, carboxyl, or lower alkyl sulfonyl;

wherein:
substituted phenyl means a phenyl group in which one or more of the phenyl hydrogens has been replaced by the same or different substituents selected from the group consisting of halo, lower alkyl, halo lower alkyl, nitro, amino, acylamino, hydroxy, lower alkoxy, phenyl lower alkoxy, acyloxy, cyano, halo lower alkoxy or lower alkyl sulfonyl;

and wherein:
substituted pyridyl means a pyridyl group in which one or more of the hydrogens on pyridyl ring carbons have been replaced by substituents as given above with respect to substituted phenyl;
or a pharmaceutically acceptable acid addition salt thereof.

16. A blood pressure lowering composition comprising an effective blood pressure lowering amount of a compound according to claim 1, 6, 10 or 11 together with a pharmaceutically acceptable carrier.